US012605211B2

(12) United States Patent　　　　　(10) Patent No.: US 12,605,211 B2
Murugappan et al.　　　　　　　　　　　(45) Date of Patent: Apr. 21, 2026

(54) METHOD AND SYSTEM FOR FACILITATING REMOTE PRESENTATION OR INTERACTION

(71) Applicant: Intuitive Surgical Operations, Inc., Sunnyvale, CA (US)

(72) Inventors: Sundar Murugappan, Danville, CA (US); Danilo Gasques Rodrigues, San Diego, CA (US); Govinda Payyavula, Sunnyvale, CA (US); Simon DiMaio, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 213 days.

(21) Appl. No.: 17/800,395

(22) PCT Filed: Mar. 30, 2021

(86) PCT No.: PCT/US2021/024999
§ 371 (c)(1),
(2) Date: Aug. 17, 2022

(87) PCT Pub. No.: WO2021/202609
PCT Pub. Date: Oct. 7, 2021

(65) Prior Publication Data
US 2023/0093342 A1　　　Mar. 23, 2023

Related U.S. Application Data

(60) Provisional application No. 63/002,102, filed on Mar. 30, 2020.

(51) Int. Cl.
*A61B 34/10*　　　(2016.01)
*A61B 34/00*　　　(2016.01)
(Continued)

(52) U.S. Cl.
CPC .............. *A61B 34/10* (2016.02); *A61B 34/20* (2016.02); *A61B 34/25* (2016.02); *A61B 34/35* (2016.02);
(Continued)

(58) Field of Classification Search
CPC .............. A61B 34/10; A61B 2034/102; A61B 2034/105; A61B 34/20; A61B 2034/2065;
(Continued)

(56) References Cited

U.S. PATENT DOCUMENTS 6,044,308　A　　3/2000　Huissoon
7,010,390　B2　　3/2006　Graf et al.
(Continued)

FOREIGN PATENT DOCUMENTS

WO　　WO-2013023130　A1　　2/2013
WO　　WO-2016069655　A1　　5/2016
(Continued)

OTHER PUBLICATIONS

Chen et al., "Virtual Object Replacement Based on Real Environments: Potential Application in Augmented Reality Systems, (Apr. 29, 2019)," Appl. Sci. 2019, 9(9), 1797. (Year: 2019).*
(Continued)

*Primary Examiner* — Keith M Raymond
*Assistant Examiner* — Ashish S. Jasani
(74) *Attorney, Agent, or Firm* — Osha Bergman Watanabe & Burton LLP

(57)　　　　　ABSTRACT
A facilitation system for facilitating remote presentation of a physical world includes a first object and an operating environment of the first object. The facilitation system includes a processing system configured to obtain an image frame depicting the physical world, identify a depiction of the first object in the image frame, and obtain a first spatial registration registering an object model with the first object
(Continued)

in the physical world. The object model is of the first object. The processing system is further configured to obtain an updated object model corresponding to the object model updated with a current state of the first object, and generate a hybrid frame using the image frame, the first spatial registration, and the updated object model. The hybrid frame includes the image frame with the depiction of the first object replaced by a depiction of the updated object model.

22 Claims, 9 Drawing Sheets

(51) Int. Cl.

| | |
|---|---|
| *A61B 34/20* | (2016.01) |
| *A61B 34/35* | (2016.01) |
| *A61B 90/00* | (2016.01) |
| *A61B 90/50* | (2016.01) |

(52) U.S. Cl.
CPC ............ *A61B 34/70* (2016.02); *A61B 90/361* (2016.02); *A61B 90/50* (2016.02); *A61B 2034/102* (2016.02); *A61B 2034/105* (2016.02); *A61B 2034/2065* (2016.02); *A61B 2090/365* (2016.02); *A61B 2090/367* (2016.02); *A61B 2090/368* (2016.02); *A61B 2090/502* (2016.02)

(58) Field of Classification Search
CPC ......... A61B 34/25; A61B 34/30; A61B 34/35; A61B 34/70; A61B 90/361; G06T 19/006
See application file for complete search history.

(56) References Cited

U.S. PATENT DOCUMENTS

| | | | |
|---|---|---|---|
| 9,259,289 | B2 | 2/2016 | Zhao et al. |
| 9,827,057 | B2 | 11/2017 | Zhao et al. |
| 10,376,318 | B2 | 8/2019 | Tsusaka et al. |
| 10,555,777 | B2 | 2/2020 | Griffiths et al. |
| 2005/0107920 | A1 | 5/2005 | Ban et al. |
| 2006/0149418 | A1 | 7/2006 | Anvari |

| | | | |
|---|---|---|---|
| 2011/0320039 | A1 | 12/2011 | Hsu et al. |
| 2013/0038707 | A1 | 2/2013 | Cunningham et al. |
| 2014/0100694 | A1 | 4/2014 | Rueckl et al. |
| 2016/0023355 | A1 | 1/2016 | Komatsu et al. |
| 2016/0030117 | A1 | 2/2016 | Mewes |
| 2016/0191887 | A1 | 6/2016 | Casas |
| 2016/0346930 | A1 | 12/2016 | Hares |
| 2017/0304021 | A1 | 10/2017 | Hathaway |
| 2019/0005848 | A1* | 1/2019 | Garcia Kilroy ........ G16H 40/67 |
| 2019/0035159 | A1 | 1/2019 | Tran et al. |
| 2019/0380792 | A1* | 12/2019 | Poltaretskyi ........ G06F 18/2163 |
| 2020/0038112 | A1 | 2/2020 | Amanatullah et al. |
| 2022/0392084 | A1 | 12/2022 | Mohareri et al. |
| 2023/0028689 | A1 | 1/2023 | Rabindran et al. |
| 2023/0050857 | A1 | 2/2023 | Allan et al. |
| 2023/0116795 | A1 | 4/2023 | Gomez et al. |
| 2023/0139402 | A1 | 5/2023 | Rabindran et al. |

FOREIGN PATENT DOCUMENTS

| | | | |
|---|---|---|---|
| WO | WO-2017066373 | A1 | 4/2017 |
| WO | WO-2018032083 | A1 | 2/2018 |
| WO | WO-2019099346 | A2 | 5/2019 |
| WO | WO-2019103954 | A1 | 5/2019 |
| WO | WO-2019139949 | A1 | 7/2019 |
| WO | WO-2020253280 | A1 | 12/2020 |
| WO | WO-2021097332 | A1 | 5/2021 |
| WO | WO-2021141920 | A1 | 7/2021 |
| WO | WO-2021150459 | A1 | 7/2021 |
| WO | WO-2021173541 | A1 | 9/2021 |
| WO | WO-2021195158 | A1 | 9/2021 |
| WO | WO-2021202609 | A1 | 10/2021 |

OTHER PUBLICATIONS

International Search Report and Written Opinion for Application No. PCT/US2021/024999, mailed on Jul. 6, 2021, 10 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Wu L., et al., "Finding the Kinematic Base Frame of a Robot by Hand-Eye Calibration Using 3D Position Data," IEEE Transactions on Automation Science and Engineering, Jan. 2017, vol. 14 (1), pp. 314-324.

* cited by examiner

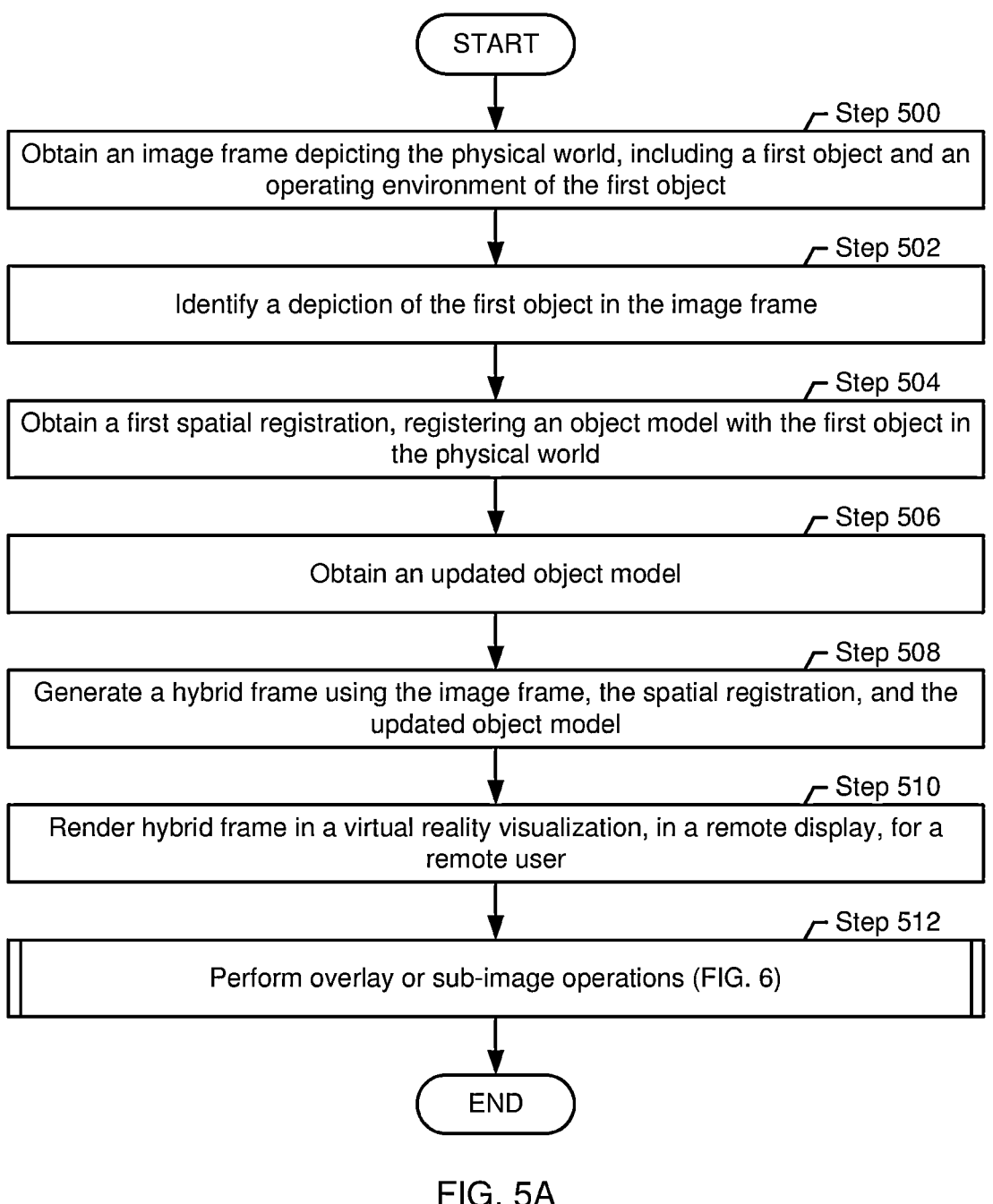

START

Step 500

Obtain an image frame depicting the physical world, including a first object and an operating environment of the first object Step 502

Identify a depiction of the first object in the image frame

Step 504

Obtain a first spatial registration, registering an object model with the first object in the physical world Step 506

Obtain an updated object model

Step 508

Generate a hybrid frame using the image frame, the spatial registration, and the updated object model Step 510

Render hybrid frame in a virtual reality visualization, in a remote display, for a remote user Step 512

Perform overlay or sub-image operations (FIG. 6)

END

FIG. 5A

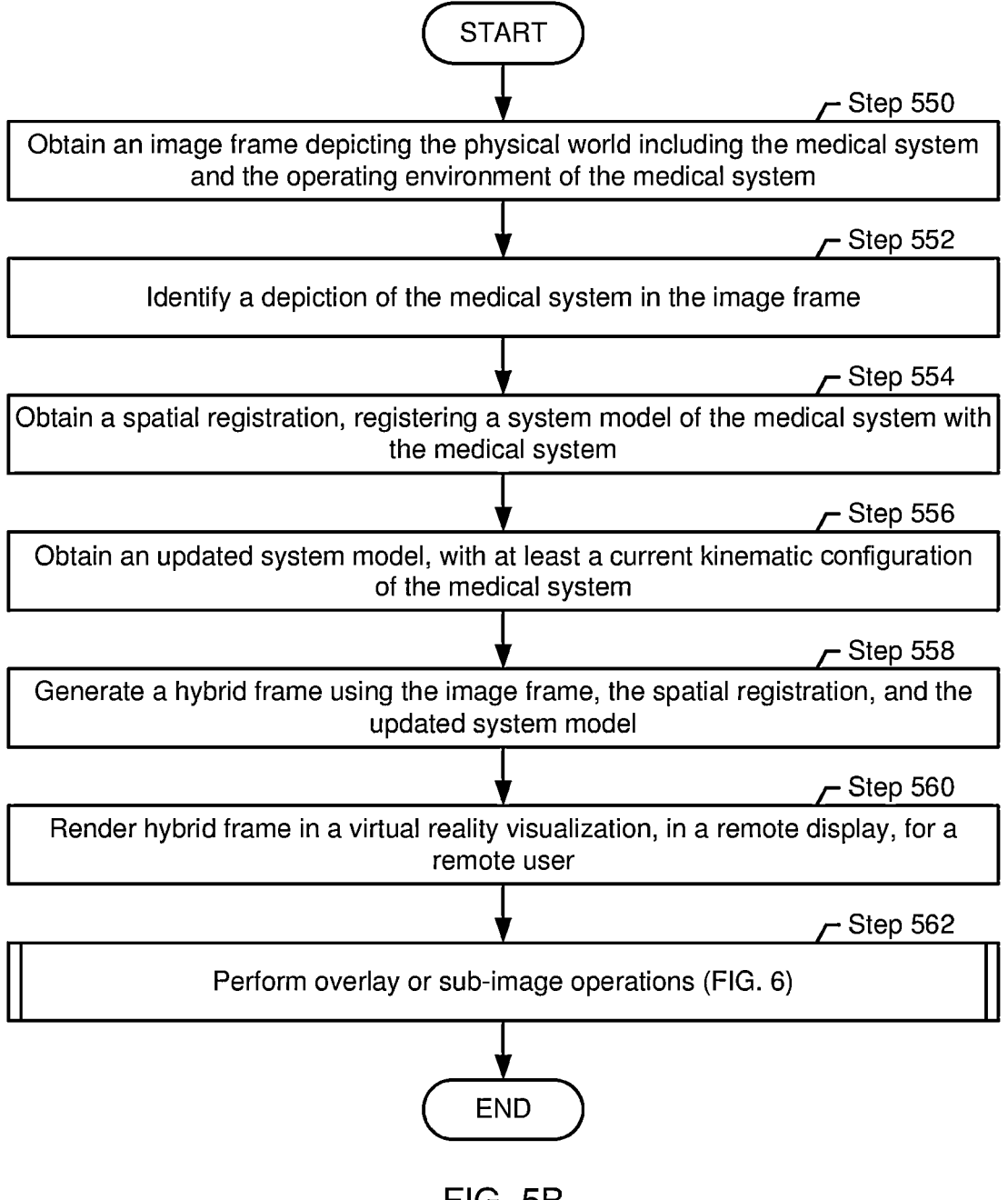

START

Step 550

Obtain an image frame depicting the physical world including the medical system and the operating environment of the medical system Step 552

Identify a depiction of the medical system in the image frame

Step 554

Obtain a spatial registration, registering a system model of the medical system with the medical system Step 556

Obtain an updated system model, with at least a current kinematic configuration of the medical system Step 558

Generate a hybrid frame using the image frame, the spatial registration, and the updated system model Step 560

Render hybrid frame in a virtual reality visualization, in a remote display, for a remote user Step 562

Perform overlay or sub-image operations (FIG. 6)

END

METHOD AND SYSTEM FOR FACILITATING REMOTE PRESENTATION OR INTERACTION

CROSS REFERENCE TO RELATED APPLICATIONS

This application is a national stage filing under 35 U.S.C. § 371 of International Patent Application Serial No. PCT/US2021/024999, filed Mar. 30, 2021, which claims benefit under 35 U.S.C. § 119(e) to U.S. Provisional Patent Application Ser. No. 63/002,102, filed on Mar. 30, 2020, the disclosures of each of which are incorporated herein by reference in their entirety.

BACKGROUND

Overview

Remote presentation and remote interaction have become more commonplace as persons interact with each other across distances short and long. For example, persons may interact with each other across the room, across cities, across countries, or across oceans and continents. Techniques that facilitate remote presentation or interaction can help enhance the interaction by improving understanding, efficiency and effectiveness of communication, reduce bandwidth requirements, and the like.

Remote presentation and remote interaction can involve robotic systems used to perform tasks at worksites. For example, a robotic system may include robotic manipulators to manipulate instruments for performing the task. Example robotic systems include industrial and recreational robotic systems. Example robotic systems also include medical robotic systems used in procedures for diagnosis, non-surgical treatment, surgical treatment, etc. As a specific example, robotic systems include minimally invasive, robotic telesurgical systems in which a surgeon may operate on a patient from bedside or a remote location.

SUMMARY

In general, in one aspect, one or more embodiments relate to a facilitation system for facilitating remote presentation of a physical world comprising a first object and an operating environment of the first object, the facilitation system comprising: a processing system configured to: obtain an image frame, the image frame depicting the physical world, identify a depiction of the first object in the image frame, obtain a first spatial registration, the first spatial registration registering an object model with the first object in the physical world, wherein the object model is of the first object, obtain an updated object model corresponding to the object model updated with a current state of the first object, and generate a hybrid frame using the image frame, the first spatial registration, and the updated object model, wherein the hybrid frame comprises the image frame with the depiction of the first object replaced by a depiction of the updated object model.

In general, in one aspect, one or more embodiments relate to a facilitation system for facilitating remote interaction, the facilitation system comprising: a processing system configured to: provide an image frame for display by a remote display, the image frame representing a physical world, obtaining a field of view of a local user of an augmented reality system local to the physical world, the local user being in the physical world, obtain, based on an input from a remote user of the remote display, a virtual sub-image to be displayed by the augmented reality system at a location in the physical world, and determine, based on the field of view and the location, whether to render an indicator to direct the field of view toward the location, and in response to a determination to render the indicator, cause rendering of the indicator by the augmented reality system.

In general, in one aspect, one or more embodiments relate to a method for operating a facilitation system for facilitating remote presentation of a physical world comprising a first object and an operating environment of the first object, the method comprising: obtaining an image frame, with a processing system of the facilitation system, the image frame depicting the physical world; identifying, with the processing system, a depiction of the first object in the image frame; obtaining, with the processing system, a first spatial registration, the first spatial registration registering an object model with the first object in the physical world, wherein the object model is of the first object; obtaining, with the processing system, an updated object model corresponding to the object model updated with a current state of the first object; and generating, with the processing system, a hybrid frame using the image frame, the first spatial registration, and the updated object model, wherein the hybrid frame comprises the image frame with the depiction of the first object replaced by the updated object model.

In general, in one aspect, one or more embodiments relate to a method for operating a facilitation system to facilitate remote interaction, the method comprising: providing, with a processing system of the facilitation system, an image frame for display by a remote display, the image frame representing a physical world, obtaining, with the processing system, a field of view of a local user of an augmented reality system local to the physical world, the local user being in the physical world; obtaining, with the processing system and based on an input from a remote user of the remote display, a virtual sub-image to be displayed by the augmented reality system at a location in the physical world; and determining, with the processing system based on the field of view and the location, whether to render an indicator to direct the field of view toward the location; and in response to a determination to render the indicator, cause a rendering of the indicator using the augmented reality system.

Other aspects will be apparent from the following description and the appended claims.

BRIEF DESCRIPTION OF DRAWINGS

FIG. 5A shows a flowchart describing methods for remote presentation or interaction, in accordance with one or more embodiments.

FIG. 5B shows a flowchart describing methods for remote presentation or interaction, in accordance with one or more embodiments.

DETAILED DESCRIPTION

Figure 1:
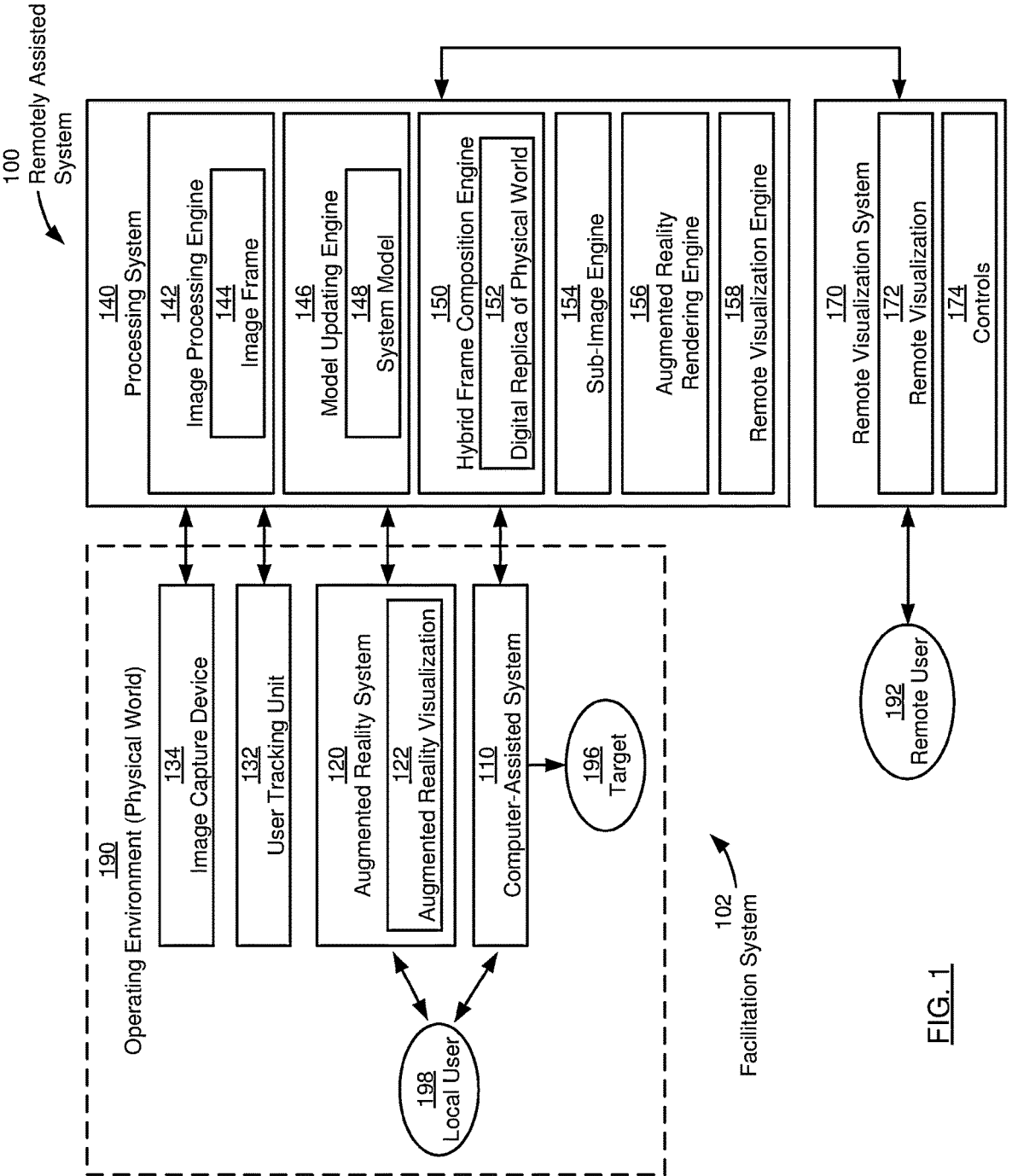
FIG. 1 shows a block diagram of a remotely assisted system, in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosed technique may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy) and performing procedures on human or animal cadavers. Further, these techniques can also be used for medical treatment or diagnosis procedures that do, or do not, include surgical aspects.

In general, embodiments of the disclosure facilitate remote presentation or interaction. Remote presentation or interaction can be used to support collaboration, training, communication, and other objectives of presentation or interaction. Remote presentation or interaction can also be used to support a local user of a robotic and/or medical system by a remote user (for example, a remote support person), or vice versa. A facilitation system may provide the remote user with a remote visualization of the robotic and/or medical system, the operating environment, and/or other components, enabling the remote user to view and visually inspect the robotic and/or medical system, the operating environment, and/or other components, for example, to detect and/or analyze a problem, or to learn.

The remote visualization may include a digital replica of the robotic and/or medical system. In other words, in the remote visualization, an image of the robotic and/or medical system may be replaced by a system model of the robotic and/or medical system. The system model may be periodically updated to reflect the current kinematic configuration (and/or other aspects of a configuration) of the actual robotic and/or medical system in the physical world.

To interact with the local user, the remote user may provide input relative to the displayed robotic and/or medical system or any other displayed component in the remote visualization, to indicate one or more sub-images to be displayed to the local user. For example, the remote user may use markers to identify elements of the robotic and/or medical system in the remote visualization, use symbols to illustrate the execution of a task, etc. The facilitation system may provide the local user with an augmented reality (AR) visualization. In the AR visualization, the local user may see the actual robotic and/or medical system in the physical world, while one or more sub-images based on the input by the remote user are visually superimposed, thereby providing guidance to the local user operating the physical world. These one or more sub-images may be rendered in the AR visualization through any appropriate technique, including as one or more overlays shown by the augmented reality system.

In one or more embodiments, the facilitation system further provides the local user with directional indicators to adjust his or her field of view to better see the one or more sub-images. This may help guide the local user's attention to the one or more sub-images.

A detailed description of systems and methods incorporating these and other features is subsequently provided. Embodiments of the disclosure may be used for various purposes including, but not limited to, facilitating technical support, remote proctoring, teaching, etc. in various fields such as manufacturing, recreation, servicing and maintenance, computer-aided medical procedures including robotic surgery, and field services in general. For example, the facilitation system may provide support for setting up, cleaning, maintaining, servicing, operation a computer-assisted medical, etc. In addition or alternatively, remote proctoring, where a more experienced user guides a less experienced user on operating a computer-assisted medical system, such as on aspects of performing a surgical procedure, may be provided.

Referring now to the drawings, in which like reference numerals represent like parts throughout the several views, FIG. 1 schematically shows a block diagram of components that enable a remotely assisted system (100). The remotely assisted system (100) may include the computer-assisted system (110), and other components that form the facilitation system (102). The facilitation system (102) may enable remote interaction between one or more local users (198) and one or more remote users (192). The remote interaction may be provided to support the local users (198), to provide learning opportunities for the remote users (192), or to provide any other interaction-related objective, such as when operating the computer-assisted system (110) in the operating environment (190). During operation, the computer-assisted system (110) may interact with a target (196) in an operating environment (190). The computer-assisted system (110) may include a computer-assisted medical system, such as a computer-assisted diagnostic system or a computer-assisted surgical system. Various components may be part of the computer-assisted system, as further discussed below.

The operating environment (190), in accordance with one or more embodiments, includes the local user (198), the computer-assisted system (110), and the target (196), and may further include an augmented reality (AR) system (120), an image capture device (134), and/or a user tracking unit (132). The facilitation system (102) includes the AR system (120), the image capture device (134), and/or the user tracking unit (132). The operating environment (190), in a medical scenario, may be an examination room, an operating room, or some other medical setting. In non-medical scenarios, the operating environment (190) may be a non-medical environment that accommodates the computer-assisted system.

In one or more embodiments, the operating environment (including the components in the operating environment) is in a physical world that is distinct from a virtual world displayed to the remote user (192), as discussed below. The virtual world may, at least partially, reflect the state of the physical world, actions performed in the physical world, etc.

The facilitation system (102) may further include a processing system (140) and a remote visualization system (170). The remote user (192) may access the facilitation system (102) using the remote visualization system (170). When using the remote visualization system (170), the remote user (192) may receive a remote visualization (172) allowing the remote user (192) to view the virtual world derived from the physical world.

Each of these elements is subsequently described. While FIG. 1 shows certain components at certain locations, those skilled in the art will recognize that the disclosure is not limited to this particular configuration. For example, while a distinction is made between the local user (198) and the remote user (192), the remote user (192) may or may not be far away from the local user. For example, the remote user (192) may be in a same room but not in the same vicinity as the local user (198) (in a surgical example, the local user may be sterile personnel able to enter the sterile space, while the remote user may be non-sterile personnel keeping outside of the sterile space), be in the same facility but in a different room from the operating environment, be in a different facility, be in a different country, or anywhere else, e.g., on a different continent. Similarly, while the processing system (140) is functionally located between various components of the facilitation system (102) in the operating environment (190), and the remote visualization system (170), the processing system may be located in whole or in part anywhere, e.g. in the operating environment, in a cloud environment, or combined with the remote visualization system (170). At least some of the components of the processing system may also be distributed. An example of an actual implementation is provided below with reference to FIG. 7.

Continuing with the discussion of the components shown in FIG. 1, in one or more medical embodiments, the computer-assisted system (110) is a medical system, such as described below with reference to FIG. 2A and FIG. 2B, or any other type of medial system. Alternatively, in other medical embodiments the computer-assisted system (110) is a non-surgical medical system (such as a non-invasive, diagnostic system). Further, as another example, the computer-assisted system (110) may be a non-medical system (such as an industrial robot).

In a medical example, the local user (198) of the computer-assisted system (110) may be a healthcare professional operating the computer-assisted system (110). For a computer-assisted system (110) including a surgical system, the healthcare professional may be a surgeon or surgical assistant.

In a medical embodiment, the target (196) can be an excised part of human or animal anatomy, a cadaver, a human, an animal, or the like. For example, a target (196) may be a patient receiving medical tests or treatment through a procedure performed by the computer-assisted system (110). In this case, the local user (198) may be a surgeon, an assistant, etc.

In one or more embodiments, the AR system (120) is a system that enables the local user (198) to see the physical world of the operating environment (190) enhanced by additional perceptual information.

The AR system (120), in one or more embodiments, is a component of the facilitation system (102). The AR system (120) may include wearable AR glasses allowing the local user (198) to see the physical world of the operating environment (190) through the glasses while also providing superimposed sub-images such as words, markers, direction arrows, labels, or other textual or graphical elements etc., in an augmented reality (AR) visualization (122). The sub-images may be any appropriate visual item; for example, a sub-image may contain text or graphics, may be static or animated, be used to telestrate, annotate, entertain, or provide any other visual interaction function. The sub-images may be provided based on input provided by the remote user (192), as discussed further below. For example, a sub-image may identify or point out a particular component of the computer-assisted system (110) by including a marker or label in the AR visualization (122) that is superimposed on the component to be pointed out. The generation of the AR visualization (122) is discussed below with reference to the flowcharts of FIG. 5A, FIG. 5B, and FIG. 6. Further, an example is provided with reference to FIG. 4.

The AR system (120) may also be based on other technologies different from AR glasses. For example, instead of enabling the local user (198) to perceive the physical world of the operating environment (190) through transparent or semi-transparent glasses, the AR visualization (122) may provide a captured image of the physical world using one or more displays. A camera image of the physical world may be shown in the display (which may include a fixed display (e.g. a monitor), a moveable display (e.g. a tablet computer), and/or a wearable display (e.g. a head mounted display), and the sub-images may be added directly to the image in the display.

The user tracking unit (132), in one or more embodiments, is a component of the facilitation system (102) and enables the tracking of the local user (198) in the operating environment (190). The user tracking unit (132) may provide information about the local user's (198) position and/or orientation in the operating environment (190). In one or more embodiments, the user tracking unit (132) provides a head orientation and/or gaze, enabling the facilitation system (102) to determine the local user's field of view and/or gaze direction.

Various tracking technologies may be used. For example, an image-based approach may use image data obtained from the image capture device (134). Other approaches may use data from inertia-based tracking, GPS tracking, etc. if available, e.g., such as when the AR system (120) includes these sensors in AR glasses or some other component. In some embodiments, the user tracking also includes eye tracking of eyes of the user. Tracking information for the local user (198) may be used for various purposes. For example, when the local user (198) wears AR glasses, sub-images that are superimposed on the physical world seen through the AR glasses may be periodically updated to keep the sub-images in alignment with the physical world, in presence of movement by the local user (198) of his or her field of view. Further, tracking information may be used to determine whether a sub-image being provided by the remote user (192) is in the field of view of the local user (198). Methods enabling these functionalities are discussed below with reference to the flowcharts of FIG. 5A, FIG. 5B, and FIG. 6.

The image capture device (134), in one or more embodiments, is a component of the facilitation system (102), and captures image frames or sequences of image frames (e.g. as a set of stills or as videos) of the operating environment (190) and/or the computer-assisted system (110) in the operating environment (190). In one embodiment, the image capture device (134) provides two-dimensional (2D) images. In another embodiment, the image capturing device (134) provides three-dimensional (3D) images. The image capture device may include a 3D depth sensor operating based on time-of-flight principles or any other principle suitable for generating 3D images at the desired spatial and temporal resolution. The image capture device (134) may alternatively, or in addition, include a combination of an RGB or infrared camera and any type of 3D-depth sensing camera such as LIDAR. The raw output of the image capture device (134), obtained at an instant in time, may be a 3D point cloud. Subsequently processing may produce an image frame that includes a 3D mesh, representing the captured operating environment (190). Methods for processing the image frame are discussed below with reference to the flowcharts of FIG. 5A and FIG. 5B.

In one embodiment, the image capture device (134) is a component of the AR system (120). More specifically, the AR system (120) (such as through AR glasses if a part of the AR system), in accordance with one or more embodiments, may be equipped with a built-in 3D depth sensor and/or other image sensor. The AR system (120) (such as through AR glasses if part of the AR system) may be equipped with head tracking to enable registration of the captured image data with the physical world. Alternatively, the image capture device (134) may be mounted elsewhere, e.g., on a wall, ceiling, etc.

As an alternative, or in addition to, the image capture device (134), other types of operating environment sensors may be used. For example, one or more laser scanners, ultrasound scanners, etc. may be used. While the image capture device (134), in accordance with one or more embodiments provides 3D data, a color or grayscale image data is not necessarily captured.

While not shown in FIG. 1, the operating environment (190) may include additional components. For example, the operating environment (190) may include other objects, in addition to the computer-assisted system (110). The other objects may be physically separate from the computer-assisted system. Examples for other objects include, but are not limited to tables, cabinets, mayo stands, machinery, operator stations, supplies, other equipment such as machinery, humans, animals, supplies, etc.

The facilitation system (102) includes the processing system (140). And, in one or more embodiments, the processing system (140) includes an image processing engine (142), a model updating engine (146), a hybrid frame composition engine (150), a sub-image engine (154), an augmented reality rendering engine (156), and/or a remote visualization engine (158).

The processing system may include other components, without departing from the disclosure. While the image processing engine (142), the model updating engine (146), the hybrid frame composition engine (150), the sub-image engine (154), the augmented reality rendering engine (156), and the remote visualization engine (158) are shown as grouped to form the processing system (140), those skilled in the art will appreciate that, in various embodiments, the processing system (140) may include a subset of these components, or include one or more additional components. Further, the components may all exist in the same physical space (e.g. in a same physical system containing processors and instructions that form the processing system), or one or more of these components may be arranged differently, e.g., in a distributed manner, such as partially in the cloud.

The image processing engine (142) is software, hardware, and/or a combination of software and hardware configured to process an image frame (144) or sets of image frames obtained from the image capture device (134). The image processing engine (142) includes a set of machine-readable instructions (stored on a computer-readable medium) which, when executed by a computing device, perform one or more of the operations described in the flowcharts of FIG. 5A, FIG. 5B, and FIG. 6. Broadly speaking, the image processing engine (142) processes the image data provided by the image capture device (134), e.g., in the form of a point cloud, to compute an image frame (144). The image processing engine (142) may further perform additional tasks, including computer vision tasks. For example, the image processing engine may identify the computer-assisted system (110) in the image frame (144) and may replace it by a configurable system model of the computer-assisted system (110). The image processing engine (142) may be implemented on a computing device such as the computing system (242) of FIG. 2B. Some or all of the functionalities of the image processing engine (142) may be implemented on a computing device in the operating environment (190), e.g., on a processor of the image capture device (134). Some or all of the functionalities may also be implemented on a computing device that is not local to the operating environment (190), e.g., on a cloud processing system.

The model updating engine (146) is software, hardware, and/or a combination of software and hardware configured to process a system model (146). The system model (148) may be a configurable digital representation of the medical system, such as a 3D model of the computer-assisted system (110). Where the computer-assisted system is modeled using a computer-aided design (CAD) system, the CAD model may be used to provide the 3D model. In one or more embodiments, the configurable elements of the system model (148) include a kinematic configuration. Assume, for example, that the computer-assisted system (110) is a robotic manipulation system. The kinematic configuration may apply to the robotic manipulation system. The kinematic configuration may further apply to a user control system and/or other components associated with the computer-assisted system. Examples of these components are described below with reference to FIG. 2A and FIG. 2B. Joint positions and/or orientations may be used to specify parts of the kinematic configuration or the entire kinematic configuration. Other configurable elements may include, but are not limited to, indicator lights (color, status (blinking vs constant), status displays, sound emitters (beeps, messages) of the computer-assisted system (110), etc. Object models representing objects, person models representing persons, and/or other models representing other objects in the operating environment may be processed in a similar manner.

Figure 6:
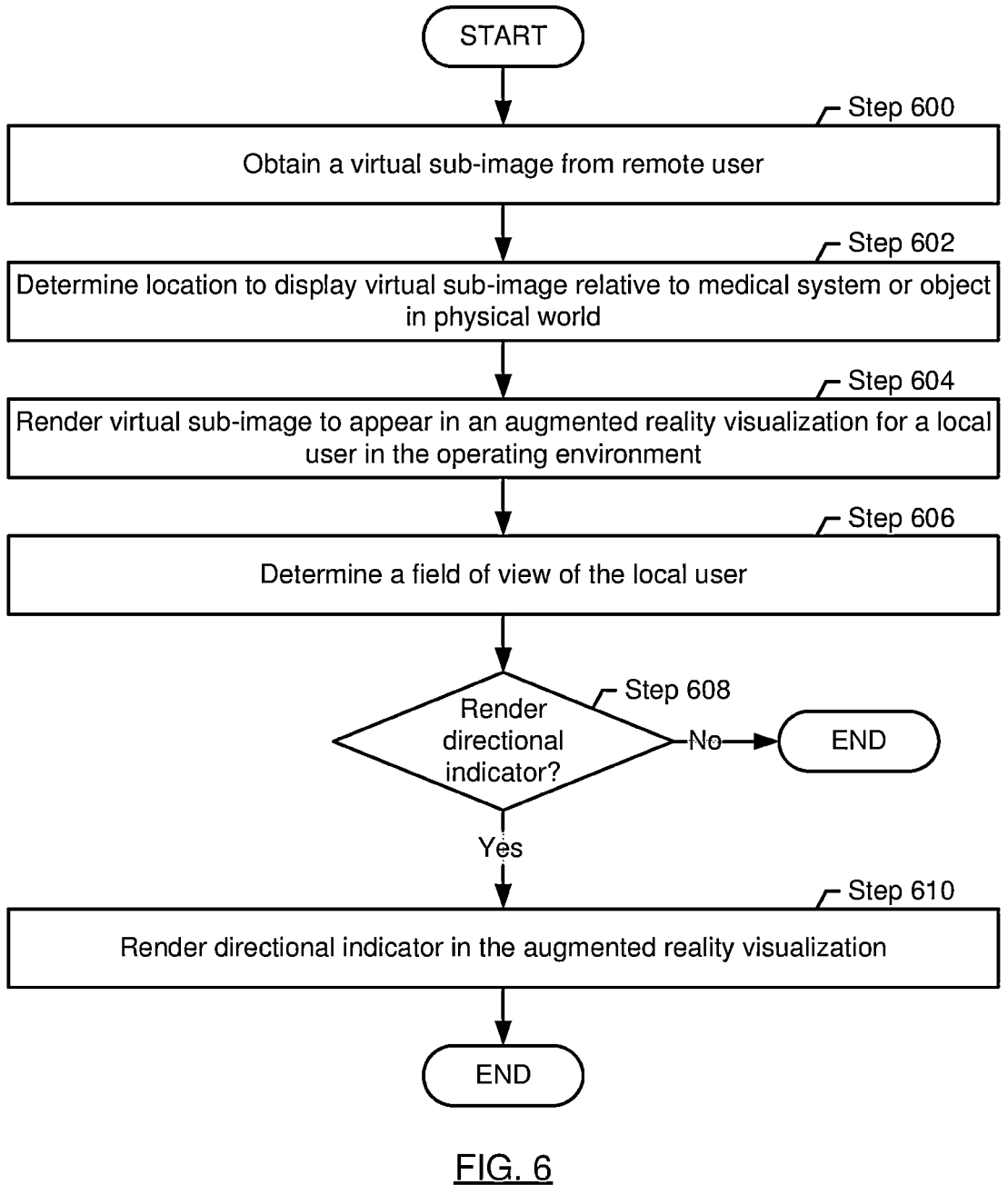
FIG. 6 shows a flowchart describing methods for facilitating the displaying of a sub-image, in accordance with one or more embodiments.

The model updating engine (146) includes a set of machine-readable instructions (stored on a computer-readable medium) which, when executed by a computing device, perform one or more of the operations described in the flowcharts of FIG. 5A, FIG. 5B, and FIG. 6. Broadly speaking, the processing of the system model (148) by the model updating engine (146) may involve an updating of the system model (148) to have the system model reflect a current kinematic configuration of the actual computer-assisted system (110) in the physical world. In addition, other aspects of the system model may be updated, including the indicator lights, etc. The updating may be performed based on real-time or near real-time data obtained from the computer-assisted system (110). Accordingly, the model updating engine may include a direct or indirect communication interface to receive configuration data from the computer-assisted system (110).

Figure 2A:
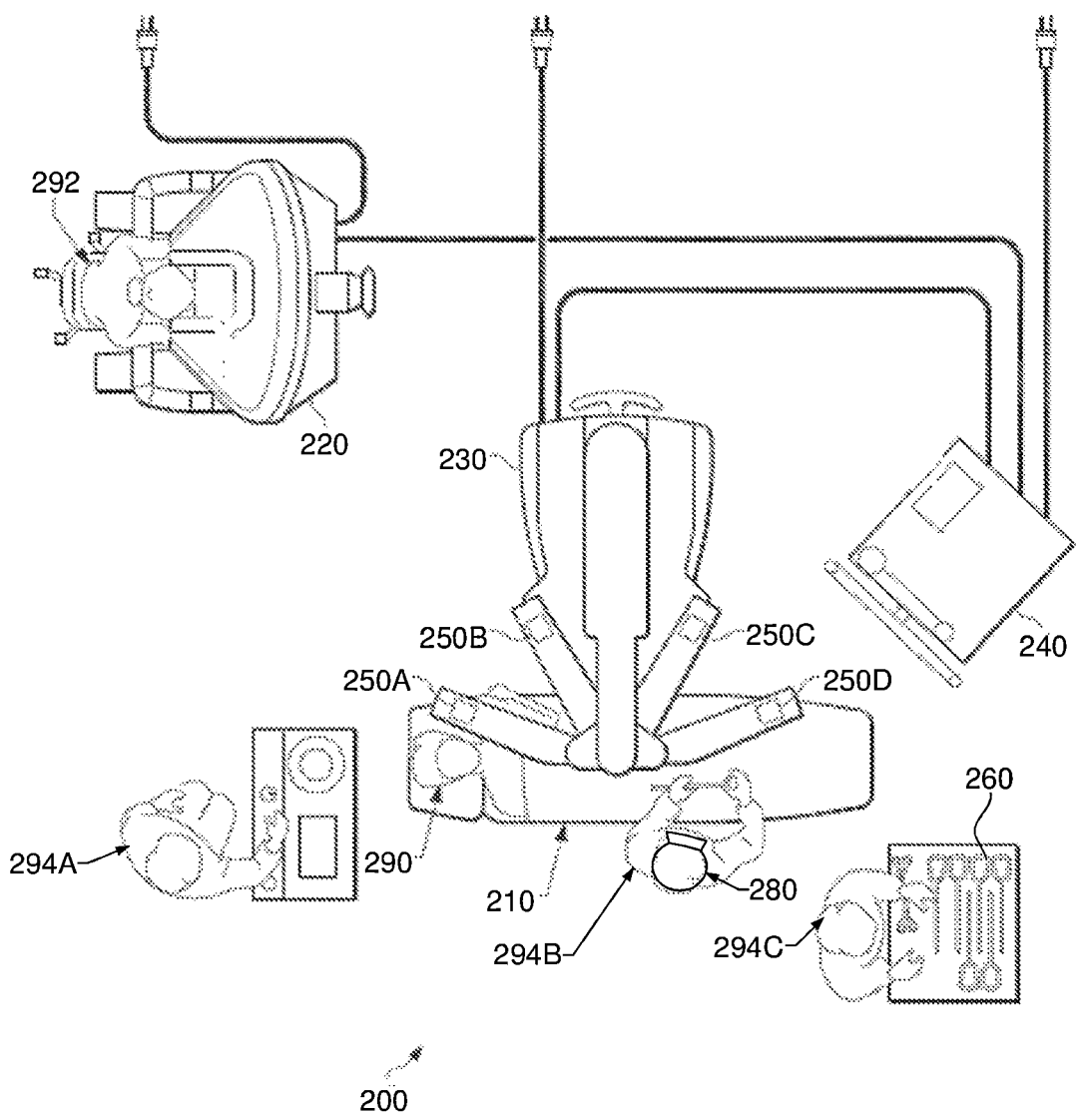
FIG. 2A shows an overhead view of a computer-assisted medical system in a robotic procedure scenario, in accordance with one or more embodiments.
Figure 2B:
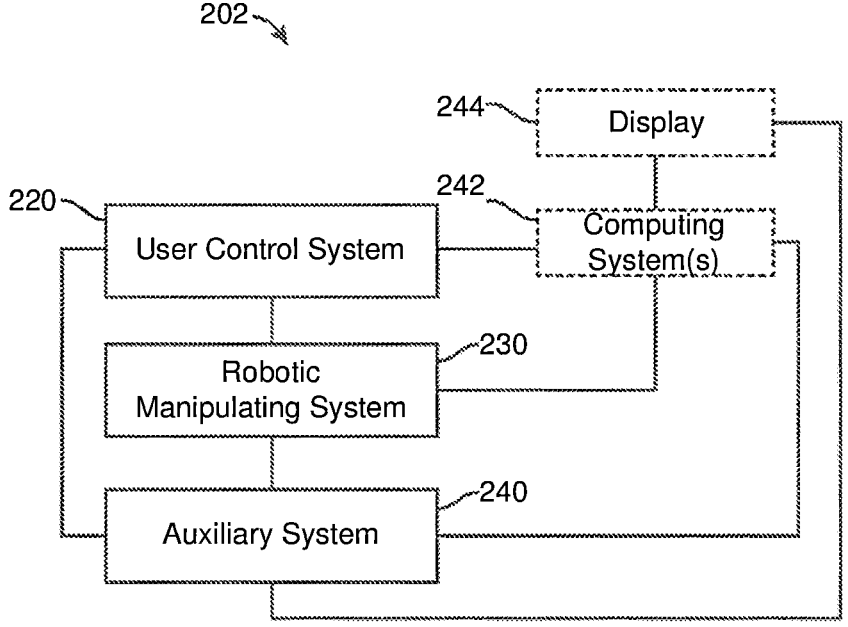
FIG. 2B diagrammatically shows various components of the robotic procedure scenario of FIG. 2A, in accordance with one or more embodiments.

The model updating engine (146) may be implemented on a computing device such as the computing system (242) of FIG. 2B. Some or all of the functionalities of the model updating engine (146) may be implemented on a cloud processing system, and/or on a computing device in the operating environment (190).

The hybrid frame composition engine (150) is software, hardware, and/or a combination of software and hardware configured to generate a digital replica (152) of the physical world. The digital replica (152), in one or more embodiments, is a digital representation of the operating environment (190), of the computer-assisted system (110), and/or of one or more objects that may exist in the operating environment. The digital replica (152) may be composed of the image frame (144) obtained by the image processing engine (142). In one or more embodiments, the area of the image frame showing the computer-assisted system (110) is replaced by the system model (148). Similarly, objects may be replaced by object models. A spatial registration may be obtained or maintained for the digital replica (152) to provide a spatial mapping of elements in the digital replica (152) and the corresponding elements in the physical world. The digital replica (152) may be used as a medium to establish a shared understanding between the local user (198) and the remote user (192). As discussed below, the digital replica may be used as a shared spatial model for both the AR visualization (122) and the remote visualization (172), although different aspects of the digital replica (152) are relied upon by the AR visualization (122) and the remote visualization (172).

The hybrid frame composition engine (150) includes a set of machine-readable instructions (stored on a computer-readable medium) which, when executed by a computing device, perform one or more of the operations described in the flowcharts of FIG. 5A, FIG. 5B, and FIG. 6. Broadly speaking, the generation of the digital replica (152) by the hybrid frame composition engine (150) may involve composing the digital replica (152) from the image frame (144), the system model (148) and/or object models. The system model (148) used in the digital replica (152) may have been updated by the model updating engine (146), prior to integration into the digital replica (152).

The hybrid frame composition engine (150) may be implemented on a computing device such as the computing system (242) of FIG. 2B. Some or all of the functionalities of the hybrid frame composition engine (150) may be implemented on a cloud processing system, and/or on a computing device in the operating environment (190).

The sub-image engine (154) is software, hardware, and/or a combination of software and hardware configured to perform sub-image operations in which sub-images are provided to the local user (198) in the AR visualization (122) based on input provided by the remote user (192) in a remote visualization (172).

The sub-image engine (154) includes a set of machine-readable instructions (stored on a computer-readable medium) which, when executed by a computing device, perform one or more of the operations described in the flowchart of FIG. 6. Broadly speaking, the sub-image engine (154) processes a virtual sub-image received from the remote user (192) in the remote visualization (172), in accordance with one or more embodiments. The virtual sub-image may be, for example, a sub-image providing guidance to the local user (198), as described further below, with reference to the flowchart of FIG. 6. A description of the rendering output resulting in the AR visualization (122) is provided below, with reference to FIG. 4.

The sub-image engine (154) may be implemented on a computing device such as the computing system (242) of FIG. 2B. Some or all of the functionalities of the sub-image engine (154) may be implemented on a cloud processing system, and/or on a computing device associated with the remote visualization system (170), discussed below.

The augmented reality rendering engine (156) is software, hardware, and/or a combination of software and hardware configured to perform the rendering for the AR visualization (122) for the local user (198). The augmented reality rendering engine (156) includes a set of machine-readable instructions (stored on a computer-readable medium) which, when executed by a computing device, perform one or more of the operations described in the flowchart of FIG. 6. The rendering may be performed for the virtual sub-images to be superimposed on the physical world, as seen by the local user (198). The rendering may involve specialized hardware, such as video display hardware.

The augmented reality rendering engine (156) may be implemented on a computing device such as the computing system (242) of FIG. 2B. Some or all of the functionalities of the augmented reality rendering engine (156) may be implemented on a processor of the AR system (120), and/or elsewhere, e.g., on a cloud processing system.

The remote visualization engine (158), is software, hardware, and/or a combination of software and hardware configured to perform the rendering for the remote visualization (172) for the remote user (192). A description of the rendering output resulting in the remote visualization (172) is provided below, with reference to FIG. 3. The remote visualization engine (158) includes a set of machine-readable instructions (stored on a computer-readable medium) which, when executed by a computing device, perform one or more of the operations described in the flowcharts of FIG. 5A and FIG. 5B. The rendering may be performed for elements of the digital replica (152). The rendering may involve specialized hardware, such as video display hardware.

The remote visualization engine (158) may be implemented on a computing device such as the computing system (242) of FIG. 2B. Some or all of the functionalities of the remote visualization engine (158) may be implemented on a processor of the remote visualization system (170), and/or elsewhere, e.g., on a cloud processing system.

The remote visualization (170), in one or more embodiments, is a component of the facilitation system (102). The remote visualization system (170) may include a display allowing the remote user (192) to see a remote visualization (172) of the physical world. The physical world may include the operating environment (190), the system model (148) of the computer-assisted system (110), and/or other components in the operating environment (190). In one or more embodiments, the remote visualization (172) is derived from the digital replica (152). What components of the digital replica (152) are rendered in the remote visualization (172) may be user-selectable. Controls (174) may enable the remote user (192) to navigate within the remote visualization (172), e.g., by zooming, panning, etc. Further, the controls (174) may enable the remote user (192) to annotate components displayed in the remote visualization (172). Sub-images may be performed using keyboard, mouse, and/or touchscreen input. The generation of the remote visualization (172) is discussed below with reference to the flowcharts of FIG. 5A and FIG. 5B, and the processing of sub-images is discussed below with reference to FIG. 6. Further, an example of a remote visualization (172) is provided in FIG. 3.

The remote user (192), accessing the remote visualization system (170) may be a support person, a proctor, a teacher, a peer, a learner, a collaborator, or any other person who may interact with the local user. As previously noted, the remote user may be physically close to or far from the local user. In one embodiment, the remote user (192) relies on the remote visualization system (170) to obtain an impression of the situation experienced by the local user (198) in the operating environment (190). For example, the remote user (192) may examine a configuration of the computer-assisted system (110) to identify the cause of a problem reported by the local user (198). The remote user (192) may have training enabling him or her to provide a problem resolution. Different remote users (192) may have different levels of training, specializations, etc. For example, one remote user may be generally familiar with various aspects of the computer-assisted system (110), whereas another remote user may have highly specialized knowledge of one particular aspect. In a scenario in which the computer-assisted system (110) is a medical system, the remote user (192) may be, for example, a robotics coordinator, a field technician, a field supervisor, a specialist, or an expert.

FIG. 2A shows an overhead view of a computer-assisted medical system (200) in a robotic procedure scenario. The components shown in FIG. 2A may be located in the operating environment (190) of FIG. 1. The computer-assisted medical system (200) may correspond to the computer-assisted system (110) of FIG. 1. While in FIG. 2A, a minimally invasive robotic surgical system is shown as the computer-assisted medical system (200), the following description is applicable to other scenarios and systems, e.g., non-surgical scenarios or systems, non-medical scenarios or computer-assisted systems, etc.

In the example, a diagnostic or surgical procedure is performed on a patient (290) who is lying down on an operating table (210). The system may include a user control system (220) for use by an operator (292) (e.g., a clinician such as a surgeon) during the procedure. One or more assistants (294A, 294B, 294C) may also participate in the procedure. The computer-assisted medical system (200) may further include a robotic manipulating system (230) (e.g., a patient-side robotic device) and an auxiliary system (240). The robotic manipulating system (230) may include at least one manipulator arm (250A, 250B, 250C, 250D), each of which may support a removably coupled tool (260) (also called instrument (260)). In the illustrated procedure, the tool (260) may enter the body of the patient (290) through a natural orifice such as the throat or anus, or through an incision, while the operator (292) views the worksite (e.g., a surgical site in the surgical scenario) through the user control system (220). An image of the worksite may be obtained by an imaging device (e.g., an endoscope, an optical camera, or an ultrasonic probe), i.e., a tool (260) used for imaging the worksite, which may be manipulated by the robotic manipulating system (230) so as to position and orient the imaging device. The auxiliary system (240) may be used to process the images of the worksite for display to the operator (292) through the user control system (220) or other display systems located locally or remotely from the procedure. The number of tools (260) used at one time generally depends on the task and space constraints, among other factors. If it is appropriate to change, clean, inspect, or reload one or more of the tools (260) being used during a procedure, an assistant (294A, 294B, 294C) may remove the tool (260) from the manipulator arm (250A, 250B, 250C, 250D), and replace it with the same tool (260) or another tool (260).

In FIG. 2A, the assistant (294B) wears AR glasses (280) of the AR system (120). The AR glasses (280) may include various components of the facilitation system (102) of FIG. 1. For example, the AR glasses (280) may include not only the AR system (120), but also the user tracking unit (132) and/or the image capture device (134). Other components of the facilitation system (102) are not shown in FIG. 2A.

FIG. 2B provides a diagrammatic view (202) of the computer-assisted medical system (200). The computer-assisted medical system (200) may include one or more computing systems (242). The computing system (242) may be used to process input provided by the user control system (220) from an operator. A computing system may further be used to provide an output, e.g., a video image to the display (244). One or more computing systems (242) may further be used to control the robotic manipulating system (230).

A computing system (242) may include one or more computer processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities.

A computer processor of a computing system (242) may be an integrated circuit for processing instructions. For example, the computer processor may be one or more cores or micro-cores of a processor. The computing system (242) may also include one or more input devices, such as a touchscreen, keyboard, mouse, microphone, touchpad, electronic pen, or any other type of input device.

A communication interface of a computing system (242) may include an integrated circuit for connecting the computing system (242) to a network (not shown) (e.g., a local area network (LAN), a wide area network (WAN) such as the Internet, mobile network, or any other type of network) and/or to another device, such as another computing system (242).

Further, the computing system (242) may include one or more output devices, such as a display device (e.g., a liquid crystal display (LCD), a plasma display, touchscreen, organic LED display (OLED), projector, or other display device), a printer, a speaker, external storage, or any other output device. One or more of the output devices may be the same or different from the input device(s). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the invention.

A computing system (242) may be connected to or be a part of a network. The network may include multiple nodes. Each node may correspond to a computing system, or a group of nodes. By way of an example, embodiments of the disclosure may be implemented on a node of a distributed system that is connected to other nodes. By way of another example, embodiments of the invention may be implemented on a distributed computing system having multiple nodes, where each portion of the disclosure may be located on a different node within the distributed computing system. Further, one or more elements of the aforementioned computing system may be located at a remote location and connected to the other elements over a network.

The robotic manipulating system (230) may use a tool (260) including an imaging device, e.g., an endoscope or an ultrasonic probe, to capture images of the worksite and output the captured images to an auxiliary system (240). The auxiliary system (240) may process the captured images in a variety of ways prior to any subsequent display. For example, the auxiliary system (240) may overlay the captured images with a virtual control interface prior to displaying the combined images to the operator via the user control system (220). The robotic manipulating system (230) may output the captured images for processing outside the auxiliary system (240). One or more separate displays (244) may also be coupled with a computing system (242) and/or the auxiliary system (240) for local and/or remote display of images, such as images of the procedure site, or other related images.

Figure 3:
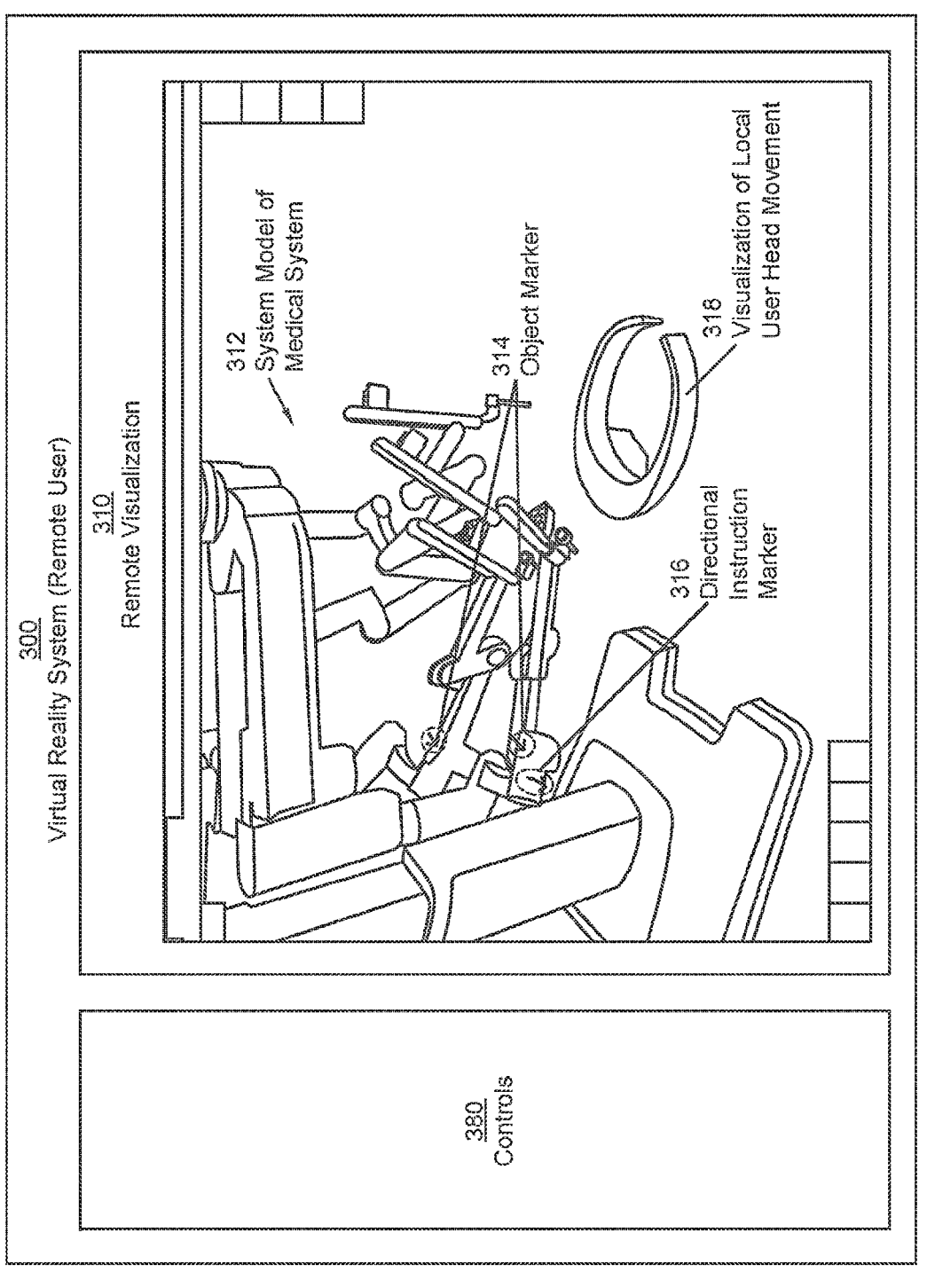
FIG. 3 shows a remote visualization system, in accordance with one or more embodiments.

Turning to FIG. 3, a remote visualization system, in accordance with one or more embodiments, is shown. The remote visualization system (300), as shown, includes a remote visualization (310), and controls (380), as previously introduced in FIG. 1. In the remote visualization (310), elements of the digital replica of the physical world are displayed. More specifically, in the example of FIG. 3, the system model (312) of a robotic manipulating system as introduced in FIG. 2, is displayed. A representation of the remainder of the operating environment is not displayed, although a point cloud, mesh, or other representation of the operating environment may be available. The representation of the remainder of the operating environment may have been automatically turned off by the remote visualization system, or disabled by the remote user, to provide a clearer view of the system model (312). The remote user may navigate within the remote visualization (310), e.g., by zooming, panning, selecting from predefined views, activating/deactivating the rendering of components, etc., using the controls (380). The rendering of these elements may be performed as described with reference to FIG. 5A and FIG. 5B, below.

As shown in FIG. 3, the remote visualization (310) further includes sub-images used by the remote user to support the local user. The sub-images, in the example of FIG. 3, include two object markers (314), and two directional instruction markers (316). The object markers (314) identify particular arm segments of the robotic manipulation system in the system model (312). The object markers (314) may have been placed by the remote user, using the controls (380). For example, the remote user may have sketched the object markers (314) or selected the object markers (314) from a library of available sub-image elements and placed them as shown, using a drag & drop operation. Other sub-images that may be placed using the controls (380) may include, but are not limited to, arrows, highlights, animations, freehand writing and/or sketches, and predefined templates specific to certain tasks or components. The purpose of the object markers (314) may be to direct the local user's attention to the identified arm segments of the robotic manipulation system in the physical world, when viewed in the local user's AR visualization. The directional instruction markers (316) illustrate movements of the arm segments identified by the object markers (314). The directional instruction markers (316) may have been placed by the remote user drawing the directional instruction markers (316) on a touch screen of the remote visualization system (300). The purpose of the directional instruction markers (316) may be to instruct the local user to adjust the orientation of the identified arm segments of the robotic manipulation system as indicated. The operations performed to enable sub-image are described below, with reference to FIG. 6.

The remote visualization (310) also includes a rendering of the local user's head location or movement. In the example, the local user's head position and orientation are represented by an illustration of the AR glasses worn by the local user, reflecting the position and orientation of the AR glasses in the physical world.

Figure 4:
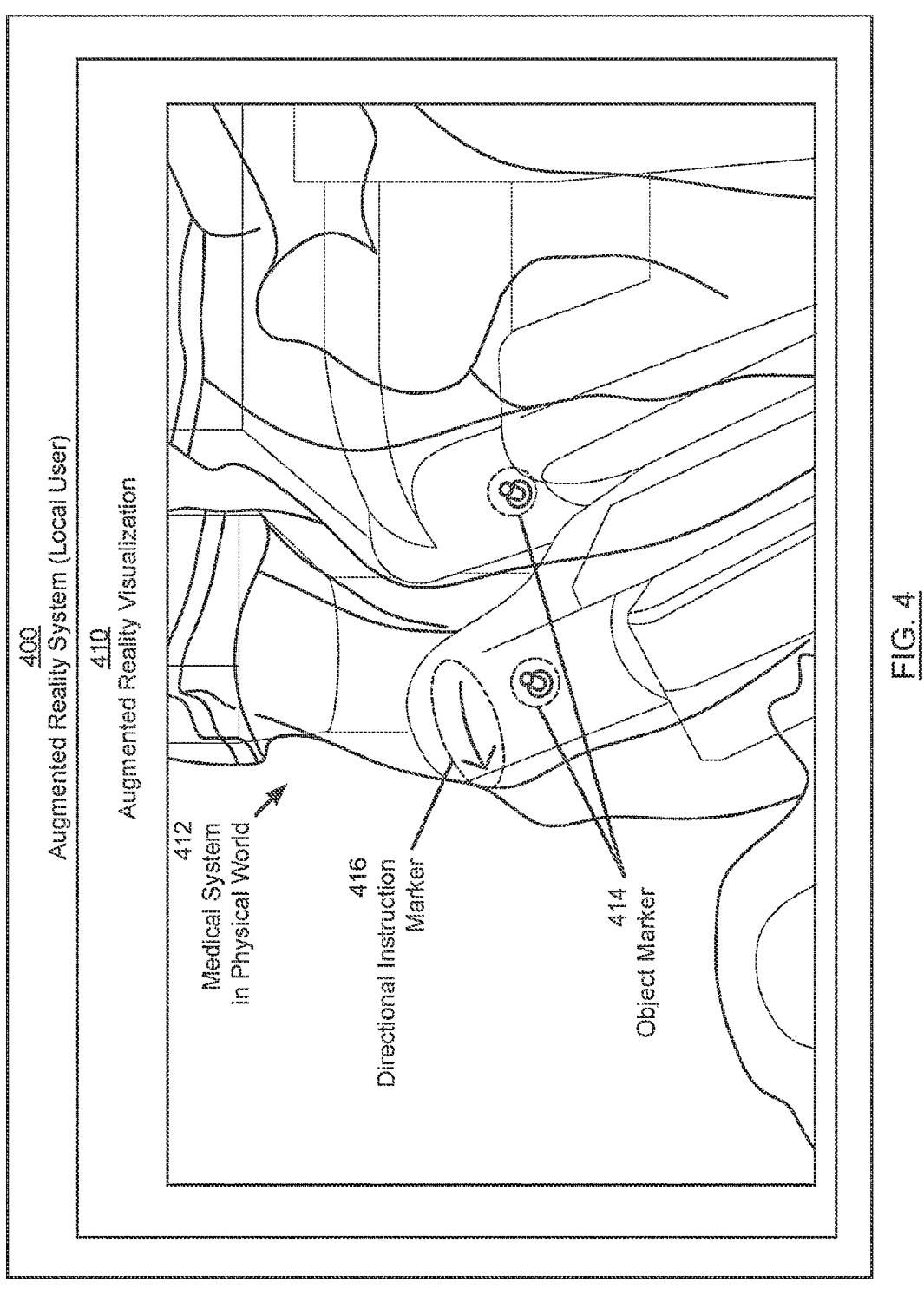
FIG. 4 shows an augmented reality system, in accordance with one or more embodiments.

Turning to FIG. 4, an augmented reality (AR) system, in accordance with one or more embodiments, is shown. The AR system (400), as shown, includes an AR visualization (410), as previously introduced in FIG. 1. In the AR visualization (410), the physical world may be seen, e.g., through transparent or semi-transparent AR glasses. In the example of FIG. 4, the local user sees the medical system (412) (e.g., the robotic manipulation system (230) of FIG. 2) against a background of the operating environment, in the physical world. The robotic manipulation system (230) is draped, e.g., loosely covered by transparent or semi-transparent plastic film. The AR visualization (410) further includes object markers (414) and directional instruction markers (416). The object markers (414) and the directional instruction markers (416) correspond to the object markers (314) and the directional instruction markers (316) in the remote visualization (310), serving as examples for sub-images having been made in the remote visualization (310) and appearing in the AR visualization (410) to assist the local user. The sub-images (e.g., the object markers (414) and the directional instruction markers (416)) appear in the AR glasses, superimposed on the physical world, seen through the AR glasses. In one or more embodiments, there is a direct correspondence between what may be seen in the AR visualization (410) and in the remote visualization (310). A spatial registration is computationally obtained or maintained between the two visualizations as discussed below with reference to the flowcharts. Accordingly, a sub-image introduced by the remote user in the remote visualization (310) appears at the correct corresponding location in the AR visualization (410), even when the field of view in the AR visualization changes as the local user moves in the physical world. More specifically, the field of view in the AR visualization (being governed by the position and orientation of the local user) is independent from the field of view in the remote visualization (being governed by zoom/pan operations performed by the remote user). While not shown in the example of FIG. 4, the AR visualization may include additional elements such as status indicators, including indicator lights (which may change color and status (blinking vs constant)), images displayed on electronic displays, status messages, acoustic information such as sounds including spatial information, spoken language, etc. The status indicators may indicate a state such as: a strength of a signal received by the system; an occurrence or continuance of an error in the system or detected by the system; a real-time event occurring in, or detected by, the system (e.g., a button press, instruments install/uninstall) or other system states. An additional example of a status indicator includes a virtual display configured to present the same image as what is rendered on a local display (e.g. a display of the user control system, a patient monitor, a display of the auxiliary system, a display of an anesthesia cart, etc.). The content to be displayed in the virtual display may be provided by the system, by a same source providing the content to the system, obtained by processing a screen capture in the image frame, etc.

Turning to the flowcharts, FIG. 5A, FIG. 5B, and FIG. 6 depict methods for facilitating remote presentation of a computer-assisted system and for facilitating remote interaction with a local user of the computer-assisted system. One or more of the steps in FIG. 5A, FIG. 5B, and FIG. 6 may be performed by various components of the systems, previously described with reference to FIG. 1, FIG. 2, FIG. 3, and FIG. 4. Some of these figures describe particular computer-assisted medical systems. However, the subsequently described methods are not limited to a particular configuration of a medical system. Instead, the methods are applicable to any type of medical system or, more generally, any type of robotic system.

While the various steps in these flowcharts are presented and described sequentially, one of ordinary skill will appreciate that some or all of the steps may be executed in different orders, may be combined or omitted, and some or all of the steps may be executed in parallel. Additional steps may further be performed. Furthermore, the steps may be performed actively or passively. For example, some steps may be performed using polling or be interrupt driven in accordance with one or more embodiments of the invention. By way of an example, determination steps may not require a processor to process an instruction unless an interrupt is received to signify that condition exists in accordance with one or more embodiments of the invention. As another example, determination steps may be performed by performing a test, such as checking a data value to test whether the value is consistent with the tested condition in accordance with one or more embodiments of the invention. Accordingly, the scope of the disclosure should not be considered limited to the specific arrangement of steps shown in FIG. 5A, FIG. 5B, and FIG. 6.

Broadly speaking, FIG. 5A, FIG. 5B, and FIG. 6 describe how a digital replica of a physical world including an operating environment and an object such as a computer-assisted device (e.g., a medical device), is used to facilitate various support tasks. More specifically, the digital replica is used as a medium to facilitate assistance to a local user of the object, by a remote user. A remote visualization of the operating environment and the object is derived from the digital replica and may be provided to the remote user. The remote user may rely on the remote visualization to remotely examine the object, an issue with the object, the operating environment, etc. The remote user may annotate elements of the digital replica to provide instructions to the user.

An augmented reality visualization may also be derived from the digital replica. The augmented reality visualization may be provided to the local user, viewed, for example, using an augmented reality (AR) display on AR glasses, a separate monitor, or some other display. In the augmented reality visualization, the sub-images may be superimposed on the actual, physical elements seen through the AR glasses. Spatial alignment of the sub-images and the physical elements is accomplished by obtaining or maintaining a spatial registration between the digital replica and the physical world, e.g., in presence of user movement.

FIG. 5A, FIG. 5B, and FIG. 6 describe methods that enable these and other functionalities. Depending on which steps of the methods of FIG. 5A, FIG. 5B, and FIG. 6 are executed, a method for facilitating remote presentation of an object (e.g. a medical system) and/or a method for facilitating remote interaction with one or more local users of an object (e.g. a medical system) may be implemented.

Turning to FIG. 5A, a method for remote presentation or interaction in accordance with one or more embodiments, is shown. The method described in reference to FIG. 5A covers the remote presentation or interaction for an object. A method that covers the remote presentation or interaction for an object of a specific type (a medical system) is described in reference to FIG. 5B.

In Step 500, an image frame is obtained. The image frame may be an image frame of a series of image frames (video), and the image frame may depict a physical world including a first object and an operating environment of the first object. The first object may be any type of object, such as a medical system, a robotic system, any type of computer-assisted system, a person, etc. In one or more embodiments, the image frame is obtained by an image capture device, which may be worn by a local user in the operating environment. Alternatively, the image frame may be captured by a camera that is stationary, in the operating environment. Obtaining the image frame may involve multiple operations which may be performed by the image capture device. At least some of the operations may alternatively be performed elsewhere. In one embodiment, the image capture device captures 3D data (such as a 3D point cloud) representing the physical world (the operating environment), including the first object, and possibly additional objects in the operating environment. The image capture device or another processing system, e.g., an image processing engine, may generate a 3D mesh (e.g., a triangular mesh) from the 3D data. In such an example, the image frame can then include the 3D mesh. Obtaining the image frame may be part of a more comprehensive process. More specifically, obtaining the image frame may be part of a simultaneous localization and mapping (SLAM) operation used for constructing a map of the operating environment while simultaneously keeping track of the local user's location in the operating environment, e.g., when the image capture device is worn by the local user who may be moving around within the operating environment. The SLAM operation thus enables an alignment to be established between the image frame and the physical world, depicted by the image frame. At least some of the subsequently described steps may depend on this spatial registration.

The image frame may be provided to other system components, either in its initial form, or after additional processing, as described below. In other words, various system components (either local or remote) may obtain the image frame provided by the image capture device.

In Step 502, the depiction of the first object is identified in the image frame. The first object may be a robotic manipulation system as previously described with reference to FIG. 2, which may further include a user control system and/or auxiliary systems. One or more of these components may be identified, in Step 502. Similarly, in Step 502, depictions of one or more objects, different from the first object, may be identified. Identified objects may include, for example, furniture, equipment, supplies, humans, structural room elements such as walls and/or, etc. An identified object may or may not be physically separate from the first object.

The detection of the first object and/or the other object(s) may be performed by a semantic segmentation of the 3D data (e.g. a 3D point cloud, a 3D mesh, etc.) in the image frame. Methods of image processing, e.g., convolutional neural networks, deep learning-based algorithms, etc., may be used for the semantic segmentation. The output of the semantic segmentation may include a classification of detected components detected in the image frame (e.g., the first object and/or other object(s)), including a location (position and/or orientation) of the detected first object and/or other object(s). In the initially described medical scenario of FIG. 2, components such as the robotic manipulation system, the user control system, the auxiliary system, the patient table, potentially the presence of the patient on the table, and third party systems such as an anesthesia cart may be detected.

Step 502 may be performed by an image processing engine. The image processing engine may be local to the operating environment, or it may be remote, e.g., hosted in a cloud environment.

In Step 504 a first spatial registration is obtained for an object model of the first object. The object model may be a configurable digital representation of the first object, such as a 3D model, as previously discussed with reference to FIG. 1. The object model may be configurable such that it is able to accurately reflect at least certain aspects of the first object, as previously discussed with reference to FIG. 1.

The first spatial registration of the object model, in one or more embodiments, is performed using the depiction of the first object identified in the image frame, and the object model. More specifically, the position and/or orientation of the first object in the image frame may be estimated based on the information derived the image frame regarding the position, orientation, and other information of the first object using image processing operations. The object model may be arranged (positioned, oriented, and/or scaled) to match the estimation of the first object in the image frame. In a model-based approach, the object model may be arranged such that features of the object model coincide with features of the first object in the image frame. For example, a matching may be performed using identifiable markers, for example, edges, points, or shapes in general. Identifying markers such as QR-code-like images may also serve as identifiable markers. In one or more embodiments, unique geometric aspects that are specific to the first object are used for the first spatial registration. For example, as shown in FIG. 2A, the robotic manipulation system (230) has unique features such as manipulator arms (250A-250D), indicator lights, etc., that can be matched to the corresponding elements of the object model. An imaging algorithm, e.g., a deep learning model, may be trained based on different example configurations of the first object. In the example of the robotic manipulation system (230) of FIG. 2A, the imaging algorithm may be trained with the robotic manipulation system having many different kinematic configurations of the manipulator arms, different indicator lights being activated, etc. Once trained offline, the imaging algorithm may be used to perform a first spatial registration of the first object with the object model. In one embodiment, the first spatial registration is performed after an updating of the spatial model as described below with reference to Step 506. Performing the first spatial registration after the updating of the spatial model may result in a particularly accurate and/or reliable spatial registration.

Similar operations may be performed for other objects that were detected when executing Step 502. Specifically, object models may be obtained for other objects, and other spatial registrations may be established to register the object models with the other objects. A target model may also be obtained for the target (e.g. a patient model may also be obtained where the target is a patient).

Step 504 may be performed by an image processing engine. The image processing engine may be local to the operating environment, or it may be remote, e.g., hosted in a cloud environment.

In Step 506, an updated object model is obtained. In one or more embodiments, the object model is updated based on the current configuration of the first object. The current configuration may be obtained from the first object, e.g., via a data interface. For example, joint positions and/or orientations may be obtained to update the kinematic configuration of the object model to reflect the current kinematic configuration of the first object (e.g., the robotic manipulation system and/or the user control system), or a person model may be updated with the current position of the person, and/or the posture of the person (e.g. including limb or torso configurations), etc. The status of indicator lights (color, status (blinking vs constant), sounds being emitted, etc. may further be obtained to update corresponding indicators of the object model.

Updating the object model based on some types of the information obtained from the first object may change the physical size, shape, position, configuration, velocity, acceleration, color, etc. of the object model (e.g., changed status light, changed kinematic configuration). Updating the object model based on some types of other information may not alter the appearance of the object model when rendered (e.g., error and status messages, signal strengths of fiberoptic signals between components of the first object, etc.)

Similar operations may be performed for other objects that were detected when executing Step 502.

Step 506 may be performed by a model updating engine. The model updating engine may be local to the operating environment, or it may be remote, e.g., hosted in a cloud environment.

In Step 508, a hybrid frame is generated, using the image frame, the first spatial registration, and the updated object model. Broadly speaking, in the hybrid frame, some depictions of objects in the image frame may be replaced by depictions of the corresponding updated object models. For example, the depiction of the first object (which may be of particular relevance), may be replaced by the depiction of the corresponding updated object model. In contrast, depictions of other objects (which may or may not be identifiable) in the image frame may not be replaced. In one or more embodiments, the hybrid frame includes the image frame, with the depiction of the first object replaced by the depiction of the updated object model and/or depictions of other objects replaced by depictions of corresponding object models. The hybrid frame may form a digital replica of the operating environment including the components in the operating environment, and in which the 3D representation (e.g., 3D point cloud, 3D mesh or other surface representation) of the first object and/or other object(s) are replaced by depictions of corresponding models that are updated to reflect the current state of the first object and/or other object(s). In the hybrid frame, the depiction of the first object, replaced by the depiction of the updated object model may serve as a spatial reference. Other elements, e.g., the object model(s) may be referenced relative to the updated object model. Similarly, the location of the image capture device used for capturing the image frame may also be referenced relative to the updated object model.

Using the spatial registrations, the digital replica of the physical world contained in the hybrid frame may remain coherent even in presence of movement of the image capture device, e.g., when the image capture device is part of a head-mounted AR system for which the spatial registrations may be updated using head tracking. One or more local users, each wearing an AR headset, may thus move around in the operating environment without disrupting the generation of the hybrid frame.

Step 508 establishes a correspondence of the digital replica and the physical world, including the operating environment, the first object, the other object(s), and/or the local user. Subsequently, the digital replica may serve as a shared model for different visualizations and/or other applications, as discussed below.

Step 508 may be performed by a hybrid frame composition engine. The hybrid frame composition engine may be local to the operating environment, or it may be remote, e.g., hosted in a cloud environment.

In Step 510, the hybrid frame is rendered in a remote visualization. The rendering may be performed for one or more remote users. The rendering may include the depiction of the updated object model. The depiction of the updated object model may be superimposed on the 3D representation (e.g., 3D point cloud, 3D mesh, or other surface representation) of the operating environment in the image frame. Alternatively, the 3D representation may be hidden. The rendering may also include the depictions of the object model(s). The rendering may further include an illustration of head location (including position and orientation) of one or more local users, e.g., based on head tracking information obtained for the one or more local users. The illustration of a head location may be an avatar or a more basic representation such as a directional symbol.

A remote user may control the view of the hybrid frame in the remote visualization, e.g., by zooming, moving in the remote visualization, etc. The remote user may further control what is visualized in the remote visualization. For example, the remote user may activate or deactivate the rendering of the 3D representation of the operating environment. When the 3D representation is deactivated, the remote user may still see the depiction of the updated object model and/or other components that are part of the hybrid frame, e.g., depictions of object models.

Step 510 may be performed by a remote visualization engine. The remote visualization engine may be local to the remote visualization system that is accessed by the remote operator. To perform the rendering, the digital replica of the physical world, including the 3D representation, the object model(s) may be streamed to the remote visualization engine, by the hybrid frame composition engine. In comparison to the initially obtained 3D representation of the operating environment, the data (e.g. the 3D mesh or other surface or point cloud representation) that is streamed may be reduced, because certain components such as the first object and/or one or more other objects are replaced by the corresponding models. To render the model(s), only the current configuration, e.g., joint angles, etc., may be streamed. An example of a rendered remote visualization is provided in FIG. 3.

In Step 512, sub-image operations are performed. The sub-image operations may enable one or more remotes user to provide guidance to, seek guidance from, or share information with, one or more local users. The rendered hybrid frame in the remote visualization may be annotated by a remote user. The sub-images may subsequently be provided to one or more local users in an augmented reality visualization. A detailed description of the steps involved in the sub-image operations is provided below with reference to FIG. 6. The execution of Step 512 is optional. Further, Step 512 may be executed without execution of all preceding steps shown in FIG. 5A. For example, a sub-image may be performed directly on the originally obtained image frame, without replacement of the first object and/or the other object(s) with corresponding models. Accordingly, it is possible to execute Step 512 while one or more of Steps 502, 504, 506, and 508 are skipped.

The method of FIG. 5A may be repeatedly executed to regularly provide one or more remote users with an updated remote visualization and/or to provide one or more local users with an updated augmented reality visualization. The steps of the method described in FIG. 5A may be executed in real-time or near-real-time, as image frames are periodically obtained.

FIG. 5B describes a remote presentation or interaction for a medical system (i.e., a particular type of object), as a specific implementation of the methodology presented and discussed with FIG. 5A. Turning to FIG. 5B, a method for remote presentation or interaction in accordance with one or more embodiments, is shown.

in Step 550, an image frame is obtained for a physical world including the medical system and an operating environment of the medical system. The operating environment depicted in the image frame may include, for example, part or all of a patient, one or more medical personnel, one or more medical tools or other medical equipment, etc. Step 550 is analogous to Step 500 with the object being a medical system, and the methodology and techniques described for Step 500 applies here as well. Thus, that text is not repeated here.

The image frame may be provided to other system components, similar to what was described in conjunction with Step 500.

In Step 552, the depiction of the medical system is identified in the image frame. The medical system may be or include a robotic manipulation system with one or more robotic manipulators including multiple joints, as previously described with reference to FIG. 2. Step 552 is analogous to Step 502 with the object being a medical system, and the methodology and techniques described for Step 502 applies here as well. Thus, that text is not repeated here. For example, Step 552 may be performed by an image processing engine, and the other identified objects may include, for example: patient monitors, mayo stands, other furniture and/or equipment, supplies, humans (e.g., a patient, a clinical staff member such as a surgeon or assistant or nurse, observers), etc. An identified object may or may not be physically separate from the medical system.

In Step 554 a spatial registration is obtained for a system model of the medical system. The system model may be a configurable digital representation of the medical system, including a physically manipulable 3D model, as previously discussed with reference to FIG. 2. The system model may be configurable such that it is able to accurately reflect at least certain aspects of the medical system, such as being configurable to reflect the physical configuration of the medical system.

The spatial registration of the system model, in one or more embodiments, is performed using the depiction of the medical system identified in the image frame, and the system model. Step 554 is analogous to Step 504 with the object being a medical system, and the object model being a system model of the medical system. The methodology and techniques described for Step 504 applies here as well, so that text is not repeated here. For example, the position and/or orientation of the medical system in the image frame may be estimated based on the information derived the image frame regarding the position, orientation, and other information of the medical system using image processing operations.

Similar spatial registration operations may be performed for other objects that were detected when executing Step 552, and register other object models with these other objects. For example, a target model may also be obtained for the target (e.g. a patient model may also be obtained where the target is a patient), and part or all of the image of the target may be replaced by a model (e.g. part or all of the patient may be replaced by part or all of a patient model). Various cues may be relied upon for the spatial registration. For example, a table position (if supporting the patient), and/or image-based cues such as a location of the patient, an arm pose, a leg pose, and/or other information may be used. Further, in some instances, additional data such as the patient's body mass index, height, or other physical characteristics may be considered. The model may also include patient health information such as blood pressure, heart rate, oxygen level, etc. The patient health information may be obtained from sensors, may be extracted from the image, and/or may be obtained from other third-party data sources. The model may also include intra-operative patient images such as CT and/or MRI scans. Other objects for which object models may be obtained include, but are not limited to, medical equipment, supplies, humans, structural room elements such as walls, floors, ceilings, etc.

In Step 556, an updated system model is obtained. In one or more embodiments, the system model is updated based on the current configuration of the medical system. The current configuration may be obtained from the medical system, e.g., via a data interface. For example, joint positions, orientations, and/or other kinematic information obtained from sensors may be obtained to update the kinematic configuration of the system model to reflect the current kinematic configuration of the medical system (e.g., the robotic manipulation system and/or the user control system). Referring to FIG. 2A, obtaining kinematic information may involve obtaining positions and/or orientations of any of the components of, or supported by, the robotic manipulation system, including: the manipulator arm(s), one or more tools supported by the robotic manipulation system, such as an imaging device, and including the individual links of these components. The positions and/or orientations of the links of the components may be computed based on position and/or orientation information of joint sensors (e.g., encoders, potentiometers, etc.). The position and/or orientation information may be used to arrange the links accordingly in a kinematic chain representing part of or the entire kinematic configuration of the robotic manipulation system. The status of indicator lights (color, operational state such as blinking vs. constant), images displayed on electronic displays, sounds being emitted, a fault status or other system states, etc. may further be obtained to update corresponding indicators of the system model.

Similar operations to obtain updated object models may be performed for other objects that were detected when executing Step 552. For example, a model of a patient may be updated based on a position of a table supporting the patent (e.g., using data obtained from the table), patient location, arm pose, leg pose (e.g., using markers locate on the patient or obtained from image processing).

Step 556 is analogous to Step 506 with the object being a medical system, and the object model being a system model of the medical system. The methodology and techniques described for Step 506 applies here as well, so that text is not repeated here.

In Step 558, a hybrid frame is generated, using the image frame, the spatial registration, and the updated system model. In one or more embodiments, the hybrid frame model includes the image frame, with the depiction of the medical system replaced by a depiction of the updated system model. Step 558 is analogous to Step 508 with the object being a medical system, and the object model being a system model of the medical system. The methodology and techniques described for Step 508 applies here as well, so that text is not repeated here. For example, the hybrid frame depict other objects replaced by corresponding depictions of other object models.

Step 558 establishes a correspondence of the digital replica and the physical world, including the operating environment, the medical system, the object(s), and/or the local user.

In Step 560, the hybrid frame is rendered in a remote visualization. The rendering may be performed for one or more remote users. The rendering may include the depiction of the updated system model. Step 560 is analogous to Step 510 with the object being a medical system, and the object model being a system model of the medical system. The methodology and techniques described for Step 510 applies here as well, so that text is not repeated here.

In Step 562, sub-image operations are performed. Step 562 is analogous to Step 512 with the object being a medical system, and the object model being a system model of the medical system. The methodology and techniques described for Step 512 applies here as well, so that text is not repeated here.

The method of FIG. 5B may be repeatedly executed to regularly provide one or more remote users with an updated remote visualization and/or to provide one or more local users with an updated augmented reality visualization. The steps of the method described in FIG. 5B may be executed in real-time or near-real-time, as image frames are periodically obtained.

Turning to FIG. 6, a method for facilitating the displaying of an overlay or a virtual sub-image, in accordance with one or more embodiments, is shown. Using the overlay or virtual sub-image, one or more remote users may provide guidance to, seek guidance from, or share information with, one or more local users, for example, when providing technical support, teaching a new task, etc. Using the described method, a remote user may annotate elements displayed in the remote visualization provided to the remote user in Step 510 of FIG. 5. The virtual sub-image(s) may then be displayed to one or more local users in the augmented reality visualization. In the augmented reality visualization, the one or more local users may see the physical world, with the virtual sub-image(s) superimposed on the actual physical elements. Because a spatial registration between the element in the physical world (e.g., medical device, objects, 3D representation of the operating environment, etc.) and the corresponding elements of the digital replica of the physical world is maintained, virtual and augmented reality visualizations may coexist, with a defined spatial mapping between the two. Accordingly, a virtual sub-image added in the remote visualization may be shown in the correct corresponding location in the augmented reality visualization. Consider, for example, a virtual sub-image added to a particular element of the system model representing the medical system in the remote visualization (e.g., the object marker in FIG. 3). The one or more local users may be near the actual, physical medical system, viewing the physical medical system through a display of an augmented reality system, such as AR glasses. Because of the continuously maintained spatial registrations, the virtual sub-image is correctly superimposed on the physical medical system by the augmented reality system (as shown, e.g., in FIG. 4).

Turning to the steps of the method, in Step 600, a virtual sub-image or overlay is obtained from a remote user. The virtual sub-image may be any kind of illustration, superimposed on the remote visualization presented to the remote user. For example, the virtual sub-image may be a symbol selected by the remote user and placed at a particular location in the remote visualization, a hand-drawn symbol, hand-written notes, typed text, highlighting, pointers or other shapes, animations selected from a toolbox, sequences of illustration to show multiple steps, etc. Other types of information may be provided as well. For example, figures, pages of manuals, web pages, audio recordings, images and video recordings, etc. may be provided. The remote user may place the virtual sub-image or overlay at a desired location, e.g., superimposed on an element that is to be annotated. Examples of virtual sub-images having been placed in the form of object markers and directional instructions are shown in FIG. 3. In one embodiment, a virtual sub-image is generated to add an avatar representing the remote user. The avatar may be any kind of a representation of the remote user providing an effective viewing location and/or viewing direction of the remote user viewing the hybrid frame, including a symbol, a photo, etc. The avatar may allow one or more local users to determine the position and viewing direction of the remote user, and may thus assist the local user(s) by providing additional context. The avatar may be controllable by the remote user. For example, a remote user may position and/or orient an avatar relative to the depiction of the object model in the hybrid frame, and the system can use the spatial registration between the object model and the corresponding object to locate a rendered avatar in the physical world. Alternatively, the position and/or orientation may be derived from parameters known the system, such as the remote user's viewing direction and zoom level. For example, the system may use the image displayed to the remote user to derive a point-of-view for the remote user, and then use that point-of-view to extrapolate an estimated viewing location and/or an estimated viewing direction for a person in the physical space to observe the same point-of-view (e.g. at the same zoom level); the system can use the estimated viewing location and/or an estimated viewing direction to locate a rendered avatar in the physical world.

Step 600 may be performed by the remote visualization engine. In other words, the remote visualization engine that renders the hybrid frame in the remote visualization may also receive input from one or more users, including input related to the virtual sub-image. The remote visualization engine may subsequently render the received virtual sub-image.

In Step 602, a location to display the virtual sub-image relative to the medical system or object in the physical world is determined. The location may be determined by projecting the sub-image onto an underlying element, as rendered in the remote visualization. Consider, for example, the remote visualization of the medical system in FIG. 3. In this two-dimensional visualization (displayed on a screen), the location of the markers (object markers, directional instruction markers) are two-dimensionally overlapping with elements of the system model representing the medical system. Accordingly, in Step 602, using a two-dimensional projection, these sub-images may be placed on the surface of these elements. More specifically, based on the projection, the virtual sub-image may be placed in a plane, tangential to the surface of the underlying element, the plane intersecting with the underlying element at the location. Any kind of element, shown in the hybrid frame, and rendered in the remote visualization, may be annotated in this manner. This includes, but is not limited to the system model of the medical system (potentially having many individual sub-elements that may be separately annotated), object models, the elements of the 3D representation of the operating environment (e.g., a 3D mesh or other surface representation, or a 3D point cloud), if displayed, etc.

The location may be determined in a different manner, if the remote visualization is three-dimensional (e.g., using a stereoscopic display). In this case, with visual depth being available, the user may three-dimensionally place the virtual sub-image, thus potentially making the projection unnecessary.

The location in the physical world may be determined based on the spatial registration of an object model with the corresponding object. In the example shown in FIG. 3, the correspondence established by the spatial registration of the system model representing the medical system and the medical system itself may be used.

In one or more embodiments, once the location is determined, an association is established between the element on which the virtual sub-image is placed, and the virtual sub-image itself. The association may ensure that when the element moves (e.g., movement of a robotic arm of the system model shown in FIG. 3), the virtual sub-image remains attached and follows the movement. The movement may be trackable, e.g., based on an updated kinematic configuration as previously described in Step 506 of FIG. 5.

Step 602 may be performed by the remote visualization engine. Alternatively, Step 602 may be performed elsewhere, e.g., by the hybrid frame composition engine.

In Step 604, the virtual sub-image is rendered to appear in the augmented reality visualization provided to one or more local users in the operating environment. The local user (s), for example wearing AR glasses, may see the physical world (the operating environment) through the AR glasses, while also perceiving the superimposed virtual sub-image rendered in the AR glasses. The physical world is, thus, augmented with the virtual sub-image. Based on the spatial registration being periodically updated (Step 504 of FIG. 5), the virtual sub-image is displayed at the proper location, even when the local user(s) moves and/or when the kinematic configuration of the medical system (or any other object) changes. An example of an augmented reality visualization is provided in FIG. 4. Those skilled in the art will recognize that the virtual sub-image may not necessarily be rendered in the augmented reality visualization. In particular, the rendering of the sub-image in the augmented reality visualization may occur only if the sub-image is in the field of view of the local user (s). For example, hypothetically assuming that the local user(s) in the scenario illustrated in FIG. 4 faces the opposite direction, looking away from the medical system, the virtual sub-image would not be rendered in the AR glasses.

Step 604 may be performed by the augmented reality rendering engine.

The subsequently discussed steps may be additionally performed to provide directional guidance to a local user. As previously discussed, the local user's field of view may not necessarily overlap with the location of the virtual sub-image. It may be desirable to spatially guide the local user to bring the virtual sub-image into the field of view of the local user, for example, because the virtual sub-image may include important information that the local user should be aware of (e.g., instructions for an error resolution).

In Step 606, the current field of view of the local user is determined. The local field of view may be determined based on head tracking information obtained for the local user. For example, AR glasses worn by the local user may be equipped with a head tracking sensor providing position and/or orientation of the local user's head in the physical world. Other geometric constraints, such as the geometry of the field of view provided by the AR glasses may be considered to determine the local user's current field of view in the physical environment.

In Step 608, a test is performed to determine whether to render a directional indicator or not. A directional indicator, intended to spatially guide the local user to adjust the field of view toward the location of the virtual sub-image, may be displayed if the location of the virtual sub-image is outside the field of view. The displaying of the directional indicator may be unnecessary if the location of the virtual sub-image is inside of the field of view. As previously discussed, head tracking information may be used to determine the current field of view in the physical world. Using the obtained or maintained spatial registrations, it may then be determined whether the location of the virtual sub-image is within the field of view or not.

If it is determined that it is unnecessary to render the directional indicator, the execution of the method of FIG. 6 may terminate. If it is determined that it is necessary to render the directional indicator, the method may proceed with the execution of Step 610.

Step 608 may be performed by a component of the augmented reality system, e.g., by the augmented reality rendering engine, or on the processing system, e.g., by the hybrid frame composition engine.

In Step 610, the directional indicator is rendered in the augmented reality visualization. The directional indicator may be rendered such that it instructs the local user to change the current field of view through the AR glasses toward the virtual sub-image. In other words, the directional indicator is computed such that following the directional indicator reduces the distance between the field of view and the virtual sub-image, to eventually have the field of view overlap with the virtual sub-image. The rendering may be visual (e.g., arrows) and/or acoustic (e.g., spoken instructions) and may include rotational instructions (e.g., to turn the head, thereby adjusting the field of view). Translational instructions (e.g., to move closer to the medical system) may also be included.

Step 610 may be performed by a component of the augmented reality system, e.g., by the augmented reality rendering engine.

The methods of FIG. 5A, FIG. 5B, and FIG. 6 are applicable for facilitating interaction between one local user and one remote user, between one local user and multiple remote users, between multiple local users and one remote user, and between multiple local users and multiple remote users. Thus, the methods are equally applicable to various scenarios, without departing from the disclosure.

In an embodiment, the described systems operate with one local user and a plurality of remote users simultaneously. A virtual sub-image may be obtained from each of the remote users. Accordingly, multiple virtual sub-images may be obtained. Each of the virtual sub-images may be processed as previously described, and a rendering of each of the virtual sub-images may be performed for the local user, by the augmented reality system. Multiple remote users may have the same or different roles. Examples roles of remote users who may use the hybrid image include: trainers or teachers, a technical or other support personnel, and observers. For example, multiple students may be observing a same procedure involving the object replaced by the object model in the hybrid image. As a specific example, multiple medical students may watch a same medical procedure being performed using a medical system by viewing the same hybrid image in which the depiction of the medical system has been replaced by a depiction of a system model of the medical system.

In an embodiment, the described systems operate with a plurality of local users and one remote user simultaneously. A virtual sub-image may be obtained from the remote user, and the virtual sub-image may be processed as previously described. A rendering of the virtual sub-image may be performed for a first local user of a first augmented reality system, but the rendering may not be performed for a second local user of a second the augmented reality system. The decision whether to render or not to render the virtual sub-image may depend on the identities of the local users. Each local user (with an identity) may have a particular role, and the role of the user may be a factor used to determine whether the virtual sub-image should be rendered nor not. Multiple local users may have the same or different roles. Examples of the remote user who may use the hybrid image include: a trainer or teacher, a technical or other support person. The remote user may observe multiple local users and interact with them in a parallel or serial manner. For example, the multiple local users may be working together to perform a procedure. As a specific example, in the case of a medical procedure being performed, the multiple local users may for a local team, and may include one or more: clinicians, assistants, interns, medical students, nurses, etc. and be supported by a remote user. The remote user may, for example, be a clinical expert, a technical support person for a medical system used by the local users, a trainee, etc.

In an embodiment, the described systems operate with multiple local users and multiple remote users simultaneously. For example, examples of remote users and local users include those recited for the above examples. As a specific example, a plurality of remote users comprising remote support personnel, may support or watch a plurality of local users working together.

In scenarios that involve multiple local and/or multiple remote users, the users may have different roles and may have different views. For example, for multiple local users, each of the local users may receive a unique augmented reality visualization that is rendered separately from augmented reality visualizations for other local users. The augmented reality visualization may be specific to the field of view of the local user, and may further be customized to render virtual sub-images and/other visual content that are of relevance to the local user (e.g., based on the identity or role of the local user, based on location in the physical world (e.g., proximity to the medical system, sterile vs nonsterile environment), based on the level of experience, the level of current workload, the level of authorization of the local user, etc.), while potentially not rendering virtual sub-images and/or other visual content that are not of relevance to the local user. Thus, in some examples, the decision whether to render or not to render the virtual sub-image may depend on the identities of the local users, the identities of the remote users, and associations between local and remote users.

Similarly, remote users may be able to individually control their virtual reality visualization, including their views, elements being shown or hidden, etc. In some instances, the shared model for select elements is maintained for some or all of the multiple local and/or remote persons. As a specific example, core elements for a procedure with a medical system such as a medical robotic procedure may include the physical locations and salient postures of clinical personnel, the robotic system, and the patient. Other elements (including real or virtual elements such as annotations) may be shared with none, a subset of, or the entirety of, the population of users. For example, a virtual element may be viewable by only the user who provided the input to generate the virtual element, by only local users, by only remote users, by only users with a particular identify (e.g. a particular name, role, group affiliation), by all users, etc. This may be set by user input, such as set by preferences indicated by the user providing the input causing the virtual element, by a user with administrator access or higher priority, etc.

Figure 7:
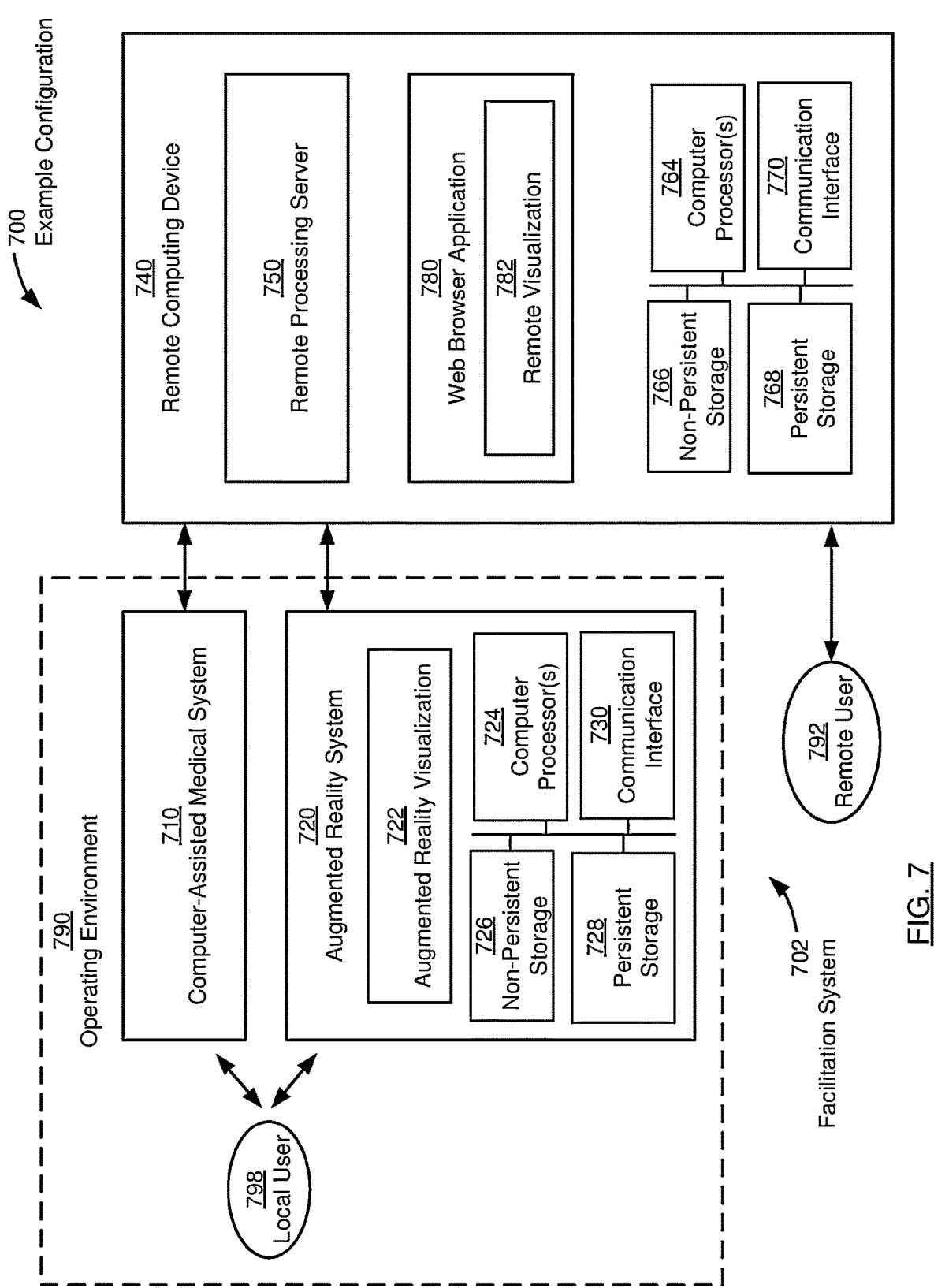
FIG. 7 shows an example implementation of a remotely assisted system, in accordance with one or more embodiments.

Turning to FIG. 7, an example configuration (700) of a remotely assisted system (710), in accordance with one or more embodiments, is shown. In FIG. 7, a local user (798) uses a computer-assisted medical system such as the robotic manipulating system (230), shown in FIG. 2. The example configuration (700) includes a facilitation system (702), including an augmented reality system (720), e.g., a set of augmented reality glasses, and a remote computing device (740). Each of these components includes or interface with at least some elements of a computing system, such as one or more computer processors (724, 764), non-persistent storage (726, 766), persistent storage (728, 768), and a communication interface (730, 770). These components may be similar to the corresponding components previously described with reference to FIG. 2B.

The local user (798) wears a component for the augmented reality system (720), such as a set of augmented reality (AR) glasses, which are equipped with a 3D depth image capture device and a display system, as previously described.

In the example of FIG. 7, image frames that include 3D data are captured by the 3D depth image device of the AR glasses. Alternatively, the image frames may be captured by a 3D depth image device located elsewhere in the operating environment.

Using the point cloud data provided by the 3D depth image capture device, a processing system of the augmented reality system (720), executing on the computer processor(s) (724) outputs a 3D triangular mesh in the format of a spatial map. The spatial map may be provided as a Wavefront OBJ file and may also include location information (e.g., based on a head tracking sensor) to anchor the spatial map to the physical world.

The spatial map including the location information is sent to the remote processing server (750) executing on the remote computing device (740) via the communication interfaces (730, 770) of the augmented reality system (720) and the remote computing device (740). The remote processing server (750), executing on the computer processor(s) (764) of the remote computing device (740) may process the spatial map to perform the spatial transformations to position and orient the spatial map for remote visualization (782) as desired by the remote user (792). The processing further includes identifying the computer-assisted medical system in the spatial map to allow replacement by a configurable 3D model.

The processing results in the generation of a hybrid frame that includes elements of the 3D representation of the operating environment, and the configurable 3D model, combined in the spatial map. Other configurable object models may be included as well. The remote processing server (750) provides the processed spatial map to the web browser application (780) executing on the processor(s) (764) of the remote computing device (740), along with the configurable 3D model. By transmitting the processed spatial map using a geometry definition file format (e.g., the Wavefront OBJ format), rather than video data being streamed, performance is optimized, and bandwidth requirements are minimized. In the example implementation, the complete spatial map is represented by the 3D data (e.g. 3D mesh) in OBJ format, and a list of 3D poses of objects (including a 4×4 matrix of float variables), and one string identifying the computer-assisted medical system (710). Using the 3D poses, the configurable 3D model may be updated to display with the proper kinematic configuration.

The remote visualization (782), generated by the web browser application (780) on the remote computing device (760) includes the processed spatial map, with the configurable 3D model inserted. The web browser application (780) may receive regular updates of the configuration of the 3D model (in the form of the 3D poses) from the remote processing server (750). The updated configuration data may be transmitted using Websocket communications. The web browser application (780) may update the displayed 3D model in the remote visualization (782), whenever updated configuration data is received. The web browser application (780) may be implemented in JavaScript-based, using libraries providing 3D graphics capabilities.

Sub-images, received from the remote user (792), are processed by the web browser application (780). More specifically, a sub-image is captured within the remote visualization (782) to determine the location in the spatial map. Subsequently, the sub-image and the identified location in the spatial map are shared to the remote processing server (750). Because the spatial map is periodically updated, the location of the sub-image maps to the proper corresponding location in the physical world of the operating environment (790), even in presence of movement of the local user (798). Subsequently, the remote processing server provides the sub-image and the location of the sub-image to the augmented reality system (720) via the communication interfaces (730, 770).

The sub-image is rendered by the augmented reality system (720) for display in the augmented reality visualization (722), e.g., in AR glasses worn by the local user (798). The sub-image may or may not be visible to the local user (798), depending on the current field of view of the local user. The field of view is determined by the augmented reality system (720) using head tracking information. In the example, the head tracking information is obtained from a head tracking sensor of the AR glasses. If the sub-image is not currently in the field of view of the local user (798), directional indicators are rendered by the augmented reality system to direct the local user toward the sub-image. The directional indicators are added to the augmented reality visualization (722), displayed to the local user (798) in the AR glasses. The operations associated with the rendering of the sub-image and/or the directional indicator are performed by the computer processor(s) (724) of the AR system (720).

Embodiments of the disclosure may have numerous applications. In one example use case, the local user encounters a problem with a robotic manipulation system. The local user has a limited understanding of the robotic manipulation system and, therefore, is unable to proceed with a procedure that is in progress.

The remote user reviews the current situation in the operating environment to understand the problem encountered by the local user, and to provide guidance for resolving the problem. The remote user, in the remote visualization as shown in FIG. 3, assesses the current configuration of the robotic manipulation system and notices that two of the four robotic manipulator arms have collided, therefore impairing further movement. The remote user concludes that mechanically reconfiguring the colliding elements of the two manipulator arms would resolve the problem, allowing the ongoing procedure to continue.

As shown in FIG. 3, the remote user places object markers to identify the elements of the robotic manipulator arms that require mechanical reconfiguration. The remote user further places directional instruction markers to indicate how the elements are to be moved to resolve the collision between the two robotic manipulator arms.

As shown in FIG. 4, the local user, in the AR visualization, sees the object marker and the direction instruction markers identifying the elements of the manipulator arm that require mechanical reconfiguration. In addition, the local and the remote user may use an audio link to verbally discuss the reconfiguration.

While a robotic surgical procedure is described in the above use case, embodiments of the disclosure may be used for many other applications, including technical support, remote proctoring, teaching, etc., in various fields such as manufacturing, robotic surgery, and field services in general.

Embodiments of the disclosure may thus improve the efficiency of remotely provided assistance. Specifically, in remote support tasks, the remote user may be able to quickly assess a local problem without extensive questioning of the local user. Confusion and/or miscommunications may be drastically reduced, in particular when dealing with more challenging support tasks and/or less experienced local users. Through the use of a digital replica that contains not only a mesh representation of the physical world, but also a (potentially highly accurate) system model of the computer-assisted system, even the smallest details that would not be available in a purely camera image-based representations may be conveyed, while not requiring significant bandwidth for data transmission. Accordingly, using embodiments of the disclosure, a very high level of remote support, typically only available through local support persons, may be provided.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A facilitation system for facilitating remote presentation of a physical world comprising a medical system with a robotic manipulator and an operating environment of the medical system, the facilitation system comprising:

a processing system configured to:

obtain an image frame, the image frame depicting the physical world;

identify a depiction of the medical system in the image frame;

obtain a first spatial registration, the first spatial registration registering a system model of the medical system with the medical system in the physical world, wherein the system model comprises a plurality of 3D objects spatially arranged based on a plurality of 3D poses;

obtain an updated system model corresponding to the system model updated with a current kinematic configuration of the robotic manipulator, wherein the current kinematic configuration comprises positions of joints of the robotic manipulator, and wherein the updating of the system model comprises updating the 3D poses from previous 3D poses based on the positions of the joints;

generate a hybrid frame using the image frame, the first spatial registration, and the updated system model, wherein the hybrid frame comprises a digital replica of the physical world, the digital replica comprising the updated system model; and transmit, by the processing system, the digital replica without the image frame, to a remote visualization system that is physically separate from the processing system, for rendering.

2. The facilitation system of claim 1, wherein the processing system is further configured to:

identify a depiction of an object in the image frame, the object physically separate from the medical system in the physical world; and determine a position of the object using data from the image frame; and wherein generating the hybrid frame further comprises replacing the depiction of the object in the image frame with a depiction of an object model at the position of the object, the object model being of the object.

3. The facilitation system of claim 1, wherein the first spatial registration is obtained using the image frame and the identified depiction of the medical system in the image frame.

4. The facilitation system of claim 2, wherein the object comprises a person, the object model comprises a person model of the person, and the object model updated with a current state of the object comprises the person model updated with a current position or posture of the person.

5. The facilitation system of claim 1, wherein the processing system is further configured to:

obtain, based on an input from a first user of the hybrid frame, a first virtual sub-image to be displayed by a first augmented reality system local to the physical world;

determine, based on the first spatial registration, a location to display the first virtual sub-image relative to the medical system in the physical world; and cause a rendering of the first virtual sub-image in the location by the first augmented reality system.

6. The facilitation system of claim 5, wherein the processing system is further configured to:

obtain, based on an input from a second user of the hybrid frame, a second virtual sub-image to be displayed by the first augmented reality system;

determine, based on the first spatial registration, a location to display the second virtual sub-image relative to the medical system in the physical world; and cause a rendering of the second virtual sub-image in the location by the first augmented reality system.

7. The facilitation system of claim 5, wherein the processing system is communicatively coupled to a plurality of augmented reality systems local to the physical world, the plurality of augmented reality systems comprising the first augmented reality system; and wherein the processing system is further configured to:

while causing the rendering of the first virtual sub-image in the location by the first augmented reality system, not cause a rendering of the first virtual sub-image by a second augmented reality system of the plurality of augmented reality systems, wherein the first augmented reality system is configured to render images for viewing by a first local user in the physical world, and wherein the second augmented reality systems is configured to render images for viewing by a second local user in the physical world.

8. The facilitation system of claim 7, wherein the processing system is further configured to:

determine to cause the rendering of the first virtual sub-image by the first augmented reality system based on an identity of the first local user or an identity of the first user of the hybrid frame; and determine to not cause the rendering of the first virtual sub-image by the second augmented reality system based on an identity of the second local user or an identity of the first user of the hybrid frame.

9. The facilitation system of claim 5, wherein the first virtual sub-image comprises a representation of an estimated viewing location or an estimated viewing direction of the first user of the hybrid frame.

10. The facilitation system of claim 5, wherein the processing system is further configured to:

determine, based on a field of view of a local user of the first augmented reality system and the location, whether to render an indicator directing the local user toward the location; and in response to a determination to render the indicator, cause rendering of the indicator by the first augmented reality system.

11. The facilitation system of claim 5, wherein the processing system is further configured to:

update the first spatial registration based on tracked head movement of a head of a local user of the first augmented reality system, wherein the first augmented reality system comprises a head-mounted augmented reality display worn by the local user, and wherein the head-mounted augmented reality display comprises a tracking sensor for tracking the head movement.

12. The facilitation system of claim 1, wherein the processing system is configured to:

obtain the updated system model by obtaining updated status indicators for the system model based on states of corresponding status indicators of the medical system, such that the depiction of the updated system model in the hybrid frame includes the updated status indicators.

13. A method for operating a facilitation system for facilitating remote presentation of a physical world comprising a medical system with a robotic manipulator and an operating environment of the medical system, the method, performed by a processing system, comprising:

obtaining an image frame, with a processing system of the facilitation system, the image frame depicting the physical world;

identifying, with the processing system, a depiction of the medical system in the image frame;

obtaining, with the processing system, a first spatial registration, the first spatial registration registering a system model of the medical system with the medical system in the physical world, wherein the system model comprises a plurality of 3D objects spatially arranged based on a plurality of 3D poses;

obtaining, with the processing system, an updated system model corresponding to the system model updated with a current kinematic configuration of the robotic manipulator, wherein the current kinematic configuration comprises positions of joints of the robotic manipulator, and wherein the updating of the system model comprises updating the 3D poses from previous 3D poses based on the positions of the joints;

generating, with the processing system, a hybrid frame using the image frame, the first spatial registration, and the updated system model, wherein the hybrid frame comprises a digital replica of the physical world, the digital replica comprising the updated system model; and transmitting, with the processing system, the digital replica without the image frame, to a remote visualization system that is physically separate from the processing system, for rendering.

14. The method of claim 13, further comprising:

identifying, with the processing system, a depiction of an object in the image frame, the object physically separate from the medical system in the physical world; and determining, with the processing system, a position of the object using data from the image frame, wherein generating the hybrid frame further comprises replacing the depiction of the object in the image frame with a depiction of an object model at the position of the object, the object model being of the object.

15. The method of claim 13, further comprising:

obtaining, with the processing system and based on an input from a first user of the hybrid frame, a first virtual sub-image to be displayed by a first augmented reality system local to the physical world;

determining, with the processing system and based on the first spatial registration, a location to display the first virtual sub-image relative to the medical system in the physical world; and causing, with the processing system, a rendering of the first virtual sub-image in the location by the first augmented reality system.

16. The method of claim 15, further comprising:

while causing the rendering of the first virtual sub-image in the location by the first augmented reality system, not causing, with the processing system, a rendering of the first virtual sub-image by a second augmented reality system, wherein the first augmented reality system is configured to render images for viewing by a first local user in the physical world, and wherein the second augmented reality systems is configured to render images for viewing by a second local user in the physical world.

17. The method of claim 15, further comprising:

obtaining, with the processing system and based on an input from a second user of the hybrid frame, a second virtual sub-image to be displayed by a second augmented reality system;

determining, with the processing system and based on the first spatial registration, a location to display the second virtual sub-image relative to the medical system in the physical world; and causing, with the processing system, a rendering of the second virtual sub-image in the location by the second augmented reality system but not by the first augmented reality system.

18. The method of claim 15, further comprising:

determining, based on a field of view of a local user of the first augmented reality system and the location, whether to render an indicator directing the local user toward the location; and in response to a determination to render the indicator, causing a rendering of the indicator by the first augmented reality system.

19. A non-transitory machine-readable medium comprising a plurality of machine-readable instructions which when executed by one or more processors associated with a facilitation system are adapted to cause the one or more processors to perform a method for operating the facilitation system for facilitating remote presentation of a physical world, the physical world comprising a medical system and an operating environment of the medical system with a robotic manipulator, the method, performed by a processing system, comprising:

obtaining an image frame, with a processing system of the facilitation system, the image frame depicting the physical world;

identifying, with the processing system, a depiction of the medical system in the image frame;

obtaining, with the processing system, a first spatial registration, the first spatial registration registering a system model with the medical system in the physical world, wherein the system model comprises a plurality of 3D objects spatially arranged based on a plurality of 3D poses;

obtaining, with the processing system, an updated system model corresponding to the system model updated with a current kinematic configuration of the robotic manipulator, wherein the current kinematic configuration comprises positions of joints of the robotic manipulator, and wherein the updating of the system model comprises updating the 3D poses from previous 3D poses based on the positions of the joints;

generating, with the processing system, a hybrid frame using the image frame, the first spatial registration, and the updated system model, wherein the hybrid frame comprises a digital replica of the physical world, the digital replica comprising system model; and transmitting, with the processing system, the digital replica without the image frame, to a remote visualization system that is physically separate from the processing system, for rendering.

20. The non-transitory machine-readable medium of claim 19, wherein the method further comprises:

obtaining, with the processing system and based on an input from a first user of the hybrid frame, a first virtual sub-image to be displayed by a first augmented reality system local to the physical world;

determining, with the processing system and based on the first spatial registration, a location to display the first virtual sub-image relative to the medical system in the physical world; and causing, with the processing system, a rendering of the first virtual sub-image in the location by the first augmented reality system.

21. The non-transitory machine-readable medium of claim 20, wherein the method further comprises:

while causing the rendering of the first virtual sub-image in the location by the first augmented reality system, not causing, with the processing system, a rendering of the first virtual sub-image by a second augmented reality system, wherein the first augmented reality system is configured to render images for viewing by a first local user in the physical world, and wherein the second augmented reality systems is configured to render images for viewing by a second local user in the physical world.

22. The non-transitory machine-readable medium of claim 20, wherein the method further comprises:

determining, based on a field of view of a local user of the first augmented reality system and the location, whether to render an indicator directing the local user toward the location; and in response to a determination to render the indicator, causing a rendering of the indicator by the first augmented reality system.

* * * * *